US010012659B2

(12) United States Patent
Nielsen

(10) Patent No.: US 10,012,659 B2
(45) Date of Patent: Jul. 3, 2018

(54) METHODS FOR DIAGNOSING IRON-RELATED PATHOLOGIES

(71) Applicant: The Arizona Board of Regents on behalf of the University of Arizona, Tucson, AZ (US)

(72) Inventor: Vance G. Nielsen, Tucson, AZ (US)

(73) Assignee: Arizona Board of Regents on behalf of the University of Arizona, Tuscon, AZ (US)

(*) Notice: Subject to any disclaimer, the term of this patent is extended or adjusted under 35 U.S.C. 154(b) by 0 days.

(21) Appl. No.: 15/124,435

(22) PCT Filed: Mar. 17, 2015

(86) PCT No.: PCT/US2015/021010
§ 371 (c)(1),
(2) Date: Sep. 8, 2016

(87) PCT Pub. No.: WO2015/142882
PCT Pub. Date: Sep. 24, 2015

(65) Prior Publication Data
US 2017/0016923 A1    Jan. 19, 2017

Related U.S. Application Data

(60) Provisional application No. 61/954,869, filed on Mar. 18, 2014.

(51) Int. Cl.
*G01N 33/49* (2006.01)
*G01N 33/86* (2006.01)

(52) U.S. Cl.
CPC ......... *G01N 33/86* (2013.01); *G01N 2800/50* (2013.01); *G01N 2800/52* (2013.01)

(58) Field of Classification Search
None
See application file for complete search history.

(56) References Cited

U.S. PATENT DOCUMENTS 8,697,747 B2 * 4/2014 Nielsen ................ A61K 31/28
514/492
2011/0268732 A1 * 11/2011 Johansson ............ A61K 31/557
424/133.1

FOREIGN PATENT DOCUMENTS

WO    2013013043    1/2013

OTHER PUBLICATIONS

Lipinski B. et al. The Role of Iron Induced Fibrin in the Pathogenesis of AD and the Protective Role of Magnesium. Frontiers in Human Neuroscience 7:Article 735, 1-11, Oct. 29, 2013. (Year: 2013).*
Nielsen V. et al. Sonoclot Based Method to Detect Iron Enhanced Coagulation. J Thrombosis Thrombolysis 42(1)1-5, Jul. 2016 (Year: 2016).*
Lipinski B. et al. Interaction of Fibrin with RBCs. Ultrastructural Pathology 36(2)79-84, Apr. 2012. (Year: 2012).*
Pretorius E. et al. A Novel Method for Assessing the Role of Iron and its Functional Chelation in Fibrin Fibril Formation. Toxicology Mechanisms and Methods 23(5)352-359, Jun. 2013. (Year: 2013).*
Arkebauer, et al., "Carbon monoxide and nitric oxide modulate a—antiplasmin and plasmin activity: role of heme", Blood Coagul Fibrinolysis 22:712-19 (2011).
Balla, et al., "Heme, heme oxygenase, and ferritin: how the vascular endothelium survives (and dies) in an iron-rich environment", Antioxid Redox Signal, 9(12):2119-37 (2007).
Bao, et al., "Plasma heme oxygenase-1 concentration is elevated in individuals with type 2 diabetes mellitus", PLoS ONE 5:e12371 (2010).
Bartoli, et al., "Hematologic markers better predict left ventricular assist device thrombosis than echocardiographic or pump parameters", Thorac Cardiovasc Surg., 62:414-18 (2014).
Benk, et al., "Effect of cannula position in the thoracic aorta with continuous left ventricular support: four-dimensional flow-sensitive magnetic resonance imaging in an in vitro model", Eur J Cardio-Thorac Surg., 44:551-8 (2013).
Bester, et al., "High ferritin levels have major effects on the morphology of erythrocytes in Alzheimer's disease", Front Aging Neurosci., 5:88 (2013).
Gaul, et al., "Chronic daily headache in hereditary hemochromatosis treated by venesection", Headache 47:926-8 (2007).
Gupta, et al., "Coagulation and inflammatory markers in Alzheimer's and vascular dementia", Int J Clin Pract 59(1):52-7 (2005).
Gupta, et al., "Neurotherapeutic effects of novel HO-1 inhibitors in vitro and in a transgenic mouse model of Alzheimer's disease", J Neurochem 131(6):778-90 (2014).
Hagen, et al., "High headache prevalence among women with hemochromatosis: the Nord-Trøndelag health study", Ann Neurol 51:786-9 (2002).
Hedblad, et al., "COHb% as a marker of cardiovascular risk in never smokers: results from a population-based cohort study", Scand J Public Health 34:609-15 (2006).
International Search Report for PCT/US2015/021010 dated Jun. 12, 2015.
Kell, et al., "Serum ferritin is an important inflammatory disease marker, as it is mainly a leakage product from damaged cells", Metallomics, 6(4):748-73 (2014).
Kobayashi, et al., "Circulating carbon monoxide level is elevated after sleep in patients with obstructive sleep apnea", Chest 134:904-10 (2008).
Kruit, et al., "Iron accumulation in deep brain nuclei in migraine: a population-based magnetic resonance imaging study", Cephalalgia 29:351-9 (2009).
Kruit, et al., "Migraine is associated with an increased risk of deep white matter lesions, subclinical posterior circulation infarcts and brain iron accumulation: the population-based MRI Camera study", Cephalalgia 30:129-36 (2010).

(Continued)

*Primary Examiner* — Ralph J Gitomer
(74) *Attorney, Agent, or Firm* — Pabst Patent Group LLP

(57) ABSTRACT

Methods for diagnosing or assisting in the diagnosis of iron-related pathologies are provided. The methods are based on the correlation of the degree of iron-specific hypercoagulability with clinical disease. One embodiment provides a method for diagnosing or assisting in diagnosing a subject having or suspected of having an iron-related pathology by analyzing a blood sample obtained from the subject to obtain viscoelastic parameters of the blood sample as the blood sample coagulates. A variation in the viscoelastic parameters of the blood sample relative to a blood sample from a healthy subject indicates the subject has or will likely develop an iron-related pathology. Subjects having an iron-related pathology have viscoelastic parameters that are indicative of enhanced coagulation and/or diminished fibrinolysis compared to the viscoelastic parameters of the blood sample from the healthy subject.

17 Claims, 15 Drawing Sheets

(56) References Cited

OTHER PUBLICATIONS

Kwon, et al., "Neuroprotective effects of valproic acid against hemin toxicity: possible involvement of the down-regulation of heme oxygenase-1 by regulating ubiquitin-proteasomal pathway", Neurochem Int 62:240-50 (2013).

Leffler, et al., "Carbon monoxide as an endogenous vascular modulator", Am J Physiol Heart Circ Physiol 301(1):H1-H11 (2011).

Lipinski, "Modification of fibrin structure as a possible cause of thrombolytic resistance", J Thromb. Thrombolysis, 29:296-298 (2010).

Lipinski, et al., "Hydroxyl radical-modified fibrinogen as a marker of thrombosis: the role of iron", Hematology, 17:241-7 (2012a).

Lipinski, et al., "Iron enhances generation of fibrin fibers in human blood: implications for pathogenesis of stroke", Microsc. Res. Tech., 75:1185-90 (2012b).

Lipinski, et al., "Novel pathway of iron induced blood coagulation: implications for diabetes mellitus and its complications", Pol. Arch. Med. Wewn, 122:115-22 (2012c).

Lipinski, et al., "The role of iron-induced fibrin in the pathogenesis of Alzheimer's disease and the protective role of magnesium", Front Hum Neurosci 7:735 (2013).

Lipinski, et at., "Iron-induced fibrin in cardiovascular disease", Curr. Neurovasc. Resi., 10:269-274 (2013b).

Madden, et al., "Baseline red blood cell osmotic fragility does not predict the degree of post-LVAD hemolys", ASAIO J., 60:524-8 (2014).

Martinez, et al., "Functional impact of oxidative posttranslational modifications on fibrinogen and fibrin clots", Free Radic. Biol. Med., 65:411-8 (2013).

Matika, et al., "Hemodialysis patients have plasmatic hypercoagulability and decreased fibrinolytic vulnerability: role of carbon monoxide", ASAIO J 60:716-21 (2014).

Nielsen, et al., "Carbon monoxide releasing molecule-2 increases the velocity of thrombus growth and strength in human plasma", Blood Coagul Fibrinolysis 20:377-80 (2009).

Nielsen, et al., "Carbon monoxide-releasing molecule-2 decreases fibrinolysis in vitro and in vivo in the rabbit", Blood Coagul Fibrinolysis 23:104-7 (2012).

Nielsen, et al., "Carbon monoxide-releasing molecule-2 enhances coagulation in rabbit plasma and decreases bleeding time in clopldogrel/aspirin-treated rabbits", Blood Coagul Fibrinolysis 22:756-9 (2011b).

Nielsen, et al., "Fibrinogen is a heme-associated, carbon monoxide sensing molecule: a preliminary report", Blood Coagul Fibrinolysis 22:443-7 (2011).

Nielsen, et al., "Increased Carbon Monoxide Production by Hemeoxygenase-1 Caused by Device-Mediated Hemolysis: Thrombotic Phantom Menace", Artif Organs 37:1008-1014 (2013b).

Nielsen, et al., "Iron and carbon monoxide enhance coagulation and attenuate fibrinolysis by different mechanisms", Blood Coagul Fibrinolysis 25(7):695-702 (2014a).

Nielsen, et al., "Iron-enhanced coagulation is attenuated by chelation: thrombelastographic and ultrastructural analysis", Blood Coagul Fibrinolysis 25:845-50 (2014b).

Nielsen, et al., "Tobacco smoke-induced hypercoagulation in human plasma: role of carbon monoxide", Blood Coagul Fibrinolysis 24:405-10 (2013).

Novack, et al., "Changes in headache frequency in premenopausal obese women with migraine after bariatric surgery: a case series", Cephalalgia 31:1336-42 (2011).

Orino, "Functional binding analysis of human fibrinogen as an iron- and heme-binding protein", Biometals, 26:789-94 (2013).

Owens, "Endogenous carbon monoxide production in disease", Clin Biochem 43:1183-8 (2010).

Panis, et al., "Differential oxidative status and immune characterization of the early and advanced stages of human breast cancer", Breast Cancer Res. Treat., 133:881-8 (2012).

Pretorius, et al., "A novel method for assessing the role of iron and its functional chelation in fibrin fibril formation: the use of scanning electron microscopy", Toxicol. Mech. Methods, 23:352-359 (2013c).

Pretorius, et al., "Differences in morphology of fibrin clots induced with thrombin and ferric ions and its pathophysiological consequences", Heart Lung Circ., 22:447-9 (2013a).

Pretorius, et al., "Novel use of scanning electron microscopy for detection of iron-induced morphological changes in human blood", Microsc Res Tech, 76:268-71 (2013b).

Pretorius, et al., "Profound morphological changes in the erythrocytes and fibrin networks of patients with hemochromatosis or with hyperferritinemia, and their normalization by iron chelators and other agents", PLoS ONE, 9:e85271 (2014).

Pretorius, et al., "Qualitative scanning electron microscopy analysis of fibrin networks and platelet abnormalities in diabetes", Blood Coagul. Fibrinolysis, 22:463-7 (2011).

Pretorius, et al., "Scanning electron microscopy of fibrin networks in rheumatoid arthritis: a qualitative analysis", Rheumatol. Int., 32:1611-5 (2012).

Segarra, et al., "Circulating levels of plasminogen activator inhibitor type-1, tissue plasminogen activator, and thrombomodulin in hemodialysis patients: biochemical correlations and role an independent predictors of coronary artery stenosis", J Am Soc Nephrol 12:1255-63 (2001).

Shacter, et al., "Oxidative modification of fibrinogen inhibits thrombin-catalyzed clot formation", Free Radio. Biol. Med., 18:815-21 (1995).

Sharma, et al., "Impaired thrombolysis: a novel cardiovascular risk factor in end-stage renal disease", Eur Heart J 34:354-63 (2013).

Smith, et al., "Detection of carboxyhemefibrinogen and methemefibrinogen in a patient with thrombosis of a HeartMate II ventricular assist device", ASAIO J 59:93-5 (2013).

Stepanenko, et al., "Retrospective hemolysis comparison between patients with centrifugal biventricular assist and left ventricular assist devices", ASAIO J 57:382-7 (2011).

Stovner, et al., "Hereditary haemochromatosis in two cousins with cluster headache", Cephalalgia 22:317-9 (2002).

Tepper, et al., "Iron deposition in pain-regulatory nuclei in episodic migraine and chronic daily headache by MRI", Headache 52:236-43 (2012).

Thompson, et al., "Heme oxygenase derived carbon monoxide and iron mediated plasmatic hypercoagulability in a patient with calcific mitral valve disease", J Thromb Thrombolysis, DOI 10.1007/s11239-014-1134-x (2014).

Trivedi, et al., "Novel thrombosis risk index as predictor of left ventricular assist device thrombosis", ASAIO J 59:380-383 (2013).

Undas, et al., "Altered fibrin clot properties in patients on long-term haemodialysis: relation to cardiovascular mortality", Nephrol Dial Transplant 23:2010-15 (2008).

Verrotti, et al., "Migraine and obesity: metabolic parameters and response to a weight loss programme", Pediatr Obes., 10(3):220-5 (2015).

Whitson, et al., "Hemolysis, pump thrombus, and neurologic events in continuous-flow left ventricular assist device recipients", Ann Thorac Surg., 97:2097-2103 (2014).

Xu, et al., "Plasma fibrinogen is associated with cognitive decline and risk for dementia in patients with mild cognitive impairment", Int J Clin Pract 62(7):1070-5 (2007).

Yeum, et al., "Biomarkers of antioxidant capacity in the hydrophilic and lipophilic compartments of human plasma", Arch. Biochem. Biophys., 430:97-103 (2004).

Yoshioka, et al., "Clinical results with Jarvik 2000 axial flow left ventricular assist device: Osaka University Experience", J Artif Organs 17(4):308-314 (2014).

Zoccali, et al., "Fibrinogen, mortality and incident cardiovascular complications in end-stage renal failure", J Intern Med 254:132-9 (2003).

\* cited by examiner

METHODS FOR DIAGNOSING IRON-RELATED PATHOLOGIES

CROSS-REFERENCE TO RELATED APPLICATIONS

This application is a 371 application of International Application No. PCT/US2015/021010, filed Mar. 17, 2015, which claims priority to and benefit of U.S. Provisional Patent Application No. 61/954,869, entitled "Methods for Diagnosing Iron-Related Pathologies" to Vance G. Nielsen, filed on Mar. 18, 2014, and where permissible is incorporated by reference in its entirety.

FIELD OF THE INVENTION

The invention is generally directed to methods for diagnosing or assisting in the diagnosis of iron-related pathologies and thrombophilia.

BACKGROUND OF THE INVENTION

Increased circulating ferritin and free iron has been found in a variety of disease states associated with thrombophilia (Kell, et al., *Metallomics*, DOI: 10.1039/c3mt00347g (2014). When iron is added to blood or plasma characteristic changes in thrombus formation are observed, which include fusion of fibrin polymers, matting, and even sheeting of fibrin (Kell, et al., *Metallomics*, DOI: 10.1039/c3mt00347g (2014); Lipinski, et al., *Pol. Arch. Med. Wewn*, 122:115-122 (2012); Lipinski, et al., *Microsc. Res. Tech.*, 75:1185-1190 (2012;); Pretorius, et al., *Microsc Res Tech*, 76:268-271 (2013); Lipinski, et at., *Curr. Neurovasc. Resi.*, 10:269-274 (2013); Pretorius, et al., *Heart Lung Circ.*, 22:447-449 (2013)). These changes form a scanning electron micrographic (SEM) signature that has also been documented in thrombi obtained from patients with diseases involving chronic iron overload, such as diabetes mellitus and rheumatoid arthritis (Kell, et al., *Metallomics*, DOI: 10.1039/c3mt00347g (2014); Lipinski, et al., *Pol. Arch. Med. Wewn*, 122:115-122 (2012); Pretorius, et al., *Blood Coagul. Fibrinolysis*, 22:463-467 (2011); Pretorius, et al., *Rheumatol. Int.*, 32:1611-1615 (2012)). With regard to mechanism, it has been posited that iron-derived hydroxyl radicals interact with fibrinogen, making it change as a substrate for thrombin, resulting in hypercoagulation and hypofibrinolysis (Kell, et al., *Metallomics*, DOI: 10.1039/c3mt00347g (2014); Lipinski, et al., *Microsc. Res. Tech.*, 75:1185-1190 (2012;); Lipinski, et al., *J Thromb. Thrombolysis*, 29:296-298 (2010); Lipinski, et al., *Hematology*, 17:241-247 (2012)). Of interest, exposing plasma to iron chelators such as deferoxamine or antioxidants significantly attenuates SEM documented changes in clots subsequently exposed to exogenous iron (Pretorius, et al., *Toxicol. Mech. Methods*, 23:352-359 (2013)). Even more importantly, plasma obtained from patients with hemochromatosis or chronic hyperferritinemia demonstrated a SEM signature similar to that of iron exposure that can be attenuated following addition of deferoxamine (Pretorius, et al., *PLoS ONE*, 9:e85271 (2014)). In sum, while not directly demonstrated, it appeared that iron-fibrinogen interactions resulted in characteristic SEM determined morphology similar to that of diseases associated with chronic iron overload and thrombophilia.

However, the concept that iron modified fibrinogen via hydroxyl radical exposure is not supported by the observation that the procoagulant properties of fibrinogen are compromised by essentially all radical species tested by other investigators (Shacter, et al., *Free Radic. Biol. Med.*, 18:815-821 (1995); Martinez, et al., *Free Radic. Biol. Med.*, 65:411-418 (2013)). Indeed, given the typical range of soluble, nonenzymatic antioxidant concentrations present in human plasma (>1600 µM) (Yeum, et al., *Arch. Biochem. Biophys.*, 430:97-103 (2004)), it is difficult to imagine that the addition of 6-30 µM ferric chloride (which markedly changes thrombus structure (Pretorius, et al., *Toxicol. Mech. Methods*, 23:352-359 (2013)) could selectively generate hydroxyl radicals that exclusively affect fibrinogen. Instead, it appeared that iron directly bound to fibrinogen in a recent study (Orino, *Biometals*, 26:789-794 (2013)). When this information is coupled with partial restoration of normal fibrin polymer architecture with iron chelation in clots derived from patients with hemochromatosis (Pretorius, et al., *PLoS ONE*, 9:e85271 (2014)), it seems more plausible that iron-fibrinogen binding and potential conformational change in the structure of fibrinogen may enhance it as a substrate for thrombin. This sort of iron-mediated phenomenon may be similar to that observed with enhancement of fibrinogen substrate characteristics following exposure to carbon monoxide (CO) (Nielsen, et al., *Blood Coagul. Fibrinolysis*, 22:443-447 (2011)). In short, the procoagulant effects of iron, a fibrinogen-binding atom, can be attenuated by introduction of deferoxamine prior to introduction of iron into plasma (Pretorius, et al., *Toxicol. Mech. Methods*, 23:352-359 (2013)), and the plasma of patients with chronic iron overload appear to be normalized following exposure to supra-pharmacological concentrations of deferoxamine (Pretorius, et al., *PLoS ONE*, 9:e85271 (2014)). The ability to prevent or reverse the effects of iron on coagulation with chelation speaks strongly for an important role of iron binding rather than radical damage as a major mechanism of iron-mediated enhancement of fibrinogen as a substrate for thrombin.

Chronic hemodialysis is also associated with significant thrombophilia (Nakamura et al., *Nephron* 58:201-204 (1991); Molino et al., *Semin Nephrol* 24:495-501 (2004); Zoccali et al., *J Intern Med* 254:132-139 (2003)). Hemodialysis patients have a high incidence of atherosclerotic disease, stroke, myocardial infarction and venous thromboembolism, and correlation of these disease states with specific hypercoagulable and hypofibrinolytic states have been made (Zoccali et al., *J Intern Med* 254:132-139 (2003); Undas et al., *Nephrol Dial Transplant* 23:2010-2015 (2008); Sharma et al., *Eur Heart J* 34:354-363 (2013)). Hemodialysis patients have been noted to have abnormal resistance to clot lysis, which has also correlated with the incidence of cardiovascular disease (Undas et al., *Nephrol Dial Transplant* 23 :2010-2015 (2008); Sharma et al., *Eur Heart J* 34:354-363 (2013); Segarra et al., *J Am Soc Nephrol* 12:1255-1263 (2001)).

Thrombophilia can also be caused by implanted devices. Left ventricular assist device (LVAD) implantation as bridge-to-transplantation (BTT) or destination therapy (DT) has become a mainstay of therapy for endstage congestive heart disease (Trivedi et al., *Ann Thorac Surg* 98:830-834 (2014); Donneyong et al., *ASAIO J* 60:294-299 (2014); Jorde et al., *J Am Coll Cardiol* 63:1751-1757 (2014)). Although the use of LVADs as BTT resulted in improved patient survival while waiting for transplantation, persistent thrombotic morbidity (e.g., stroke, pump thrombosis) still occurs in patients implanted with contemporary continuous flow LVADs despite optimized mechanical and medical therapy (Starling et al., *N Eng J Med* 370:33-40 (2014); Najjar et al., *J Heart Lung Transplant* 33:23-34 (2014);

Trivedi et al., *ASAIO J* 59:380-383 (2013)). A concerted effort to identify biochemical markers that predict a tendency towards systemic hypercoagulability or impending pump thrombosis, such as circulating brain natriuretic peptide (BNP) and lactate dehydrogenase (LDH) activity have been proposed (Trivedi et al., *ASAIO J* 59:380-383 (2013)).

With regard to LDH as a measure of hemolysis during normal operation of various devices or after pump thrombosis, typical values are displayed in Table 1 derived from recent reports (Nielsen et al., *Artif Organs* 37:1008-1014 (2013); Smith et al., *ASAIO J* 59:93-95 (2013); Stepanenko et al., *ASAIO J* 57:382-387 (2011); Madden et al., *ASAIO J* 60:524-528 (2014); Bartoli et al., *Thorac Cardiovasc Surg* 62:414-418 (2014); Yoshioka et al., *J Artif Organs* 17(4): 308-314 (2014); Whitson et al., *Ann Thorac Surg* 97:2097-2103 (2014)). There is significant device and center variability in low grade, hemolysis-generated LDH values, possibly indicative of differences in anticoagulation or blood flow characteristics dependent on surgical implantation and pump management (Inci et al., *ASAIO J* 58:373-381 (2012); Benk et al., *Eur J Cardio-Thorac Surg* 44:551-558 (2013)). This indolent but persistent process of device-mediated hemolysis is potentially biochemically important from a coagulation perspective, as free heme will upregulate heme oxygenase (Hmox, isoform 1 inducible, isoform 2 constitutive) activity and increase CO and iron release during heme catabolism (Owens *Clin Biochem* 43:1183-1188 (2010); Balla et al., *Antioxid Redox Signal* 9:2119-2137 (2007)).

TABLE 1

LDH values associated with normal LVAD operation or during pump thrombosis.

| Reference | Device | Patient Number | Mean LDH (U/L) |
| --- | --- | --- | --- |
| 7 | HMII | 11 | 700 |
| 9 | HVAD | 10 | 234 |
| 4 | HMII | 837 | 540 (normal) |
|   |      |     | 1490 (thrombosis) |
| 10 | HMII, HVAD, Jarvik 2000 | 45 | 562-704 |
| 11 | HMII, HVAD | 20 | 279 (normal) |
|   |      |     | 2954 (thrombosis) |
| 12 | Jarvik 2000 | 8 | 860 |
| 13 | HMII | 193 | 630 |

HMII = HeartMate II; HVAD = HeartWare LVAD system; Jarvik 2000 = Jarvik 2000 LVAD (Jarvik Heart Inc., New York, NY, USA); normal = normal operation; thrombosis = pump thrombosis present. All normal values were obtained at least one month after pump placement.

Iron enhances coagulation and diminishes fibrinolysis via a recently reported mechanism (Nielsen et al., *Blood Coagul Fibrinolysis* 25(7):695-702 (2014)), and iron-enhanced coagulation has been documented in hemodialysis patients and in a patient with mitral valvular stenosis (Matika et al., *ASAIO J* 60(6):716-721 (2014); Thompson et al., *J Thromb Thrombolysis* epub ahead of print (2014)). Therefore, LVAD-associated upregulation of Hmox activity could result in iron-mediated hypercoagulation and hypofibrinolysis.

While the primary focus of investigations concerning device-associated thrombophilia have focused on patient-pump interactions, the contribution of comorbidities to hypercoagulability have not been fully appreciated. Patients implanted with LVADs have been noted to be afflicted with diabetes mellitus (DM) and obesity (Trivedi et al., *Ann Thorac Surg* 98:830-834 (2014); Donneyong et al., *ASAIO J* 60:294-299 (2014); Jorde et al., *J Am Coll Cardiol* 63:1751-1757 (2014); Starling et al., *N Engl J Med* 370:33-40 (2014); Najjar et al., *J Heart Lung Transplant* 33:23-34 (2014); Whitson et al., *Ann Thorac Surg* 97:2097-2103 (2014)) and both of these conditions have been associated with enhancement of Hmox activity (Bao et al., *PLoS ONE* 5:e12371 (2010); Nielsen et al., *Blood Coagul Fibrinolysis* 26(2):200-204 (2015)). Of interest, obstructive sleep apnea (OSA), a disorder often associated with obesity, has also been demonstrated to upregulate Hmox activity (Kobayashi et al., *Chest* 134:904-910 (2008)). Consequently, while patient-device interactions are important in the development of systemic hypercoagulability, comorbid conditions may further exacerbate Hmox-associated hypercoagulability via increased release of iron into the circulation.

Alzheimer's disease (AD) is also a risk factor for thrombophilia. AD patients have been documented to have abnormally increased activated Factor VII, von Willebrand factor and prothrombin 1+2 fragment in their circulation, the substrate and result of intravascular thrombin generation (Gupta et al., *Int J Clin Pract* 59(1):52-57 (2005)). Of interest, while patients with AD were noted to have fibrinogen concentrations that on average were not abnormally increased, another work noted that patients with mild cognitive impairment were at greater risk of more rapid advancement to AD if their circulating fibrinogen concentration was >300 mg/dl (Gupta et al., *Int J Clin Pract* 59(1):52-57 (2005); Xu et al., *Int J Clin Pract* 62(7):1070-1075 (2007)). Further, patients with AD have been noted to have plasma thrombus fibrin polymerization that is structurally similar to iron-exposed plasma, and AD patients with abnormally increased ferritin concentrations have red blood cell morphological changes, with increased membrane stiffness documented with atomic force microscopy (Lipinski et al., *Front Hum Neurosci* 7:735 (2013); Bester et al., *Front Aging Neurosci* 5:88 (2013)). In sum, there is biochemical and ultrastructural evidence of circulating abnormal intravascular thrombin generation, ridged red blood cells, and consequent abnormally appearing fibrin polymerization in thrombi obtained from patients with AD, all of which could contribute to spontaneous emboli.

Given the aforementioned morphological changes in fibrin in plasma obtained from AD patients, it is of particular interest that iron enhances plasmatic coagulation kinetics and modifies ultrastructure by modulating fibrinogen (Nielsen et al., *Blood Coagul Fibrinolysis* 25(7):695-702 (2014)). Iron decreases the onset time of coagulation, enhances the speed of clot formation, and acts as an antifibrinolytic agent when tissue-type plasminogen activator (tPA) is the fibrinolysin (Nielsen et al., *Blood Coagul Fibrinolysis* 25(7):695-702 (2014)). These facts are of importance in the setting of AD, as Hmox, the endogenous enzyme system responsible for heme catabolism, has been found to be enhanced in both the brain and circulation of AD patients (Barone et al., *Neurobiol Dis* 62:144-159 (2014); Barone et al., *Free Radic Biol Med* 52(11-12):2292-2301 (2012); Di Domenico et al., *J Alzheimers Dis* 32(2):277-289 (2012); Song et al., *Exp Neurol* 254:78-89 (2014)). Further, Hmox catabolism of heme results in the release of iron (Leffler et al., *Am J Physiol Heart Circ Physiol* 301(1):H1-H11 (2011)). However, inhibition of Hmox in a murine model of AD involving a double transgenic mouse ($APP_{swe}/PS1_{\Delta E9}$) significantly diminished the behavioral deficits and neuropathological changes over time compared to mice not administered a Hmox inhibitor (Gupta et al., *J Neurochem* 131(6):778-790 (2014)). When all these data are considered as a whole, Hmox-enhanced coagulation could play a role in spontaneous thrombus formation not just in the peripheral circulation as documented by previous ultrasonic investigations but perhaps more regionally (and intensely) in the microcirculation of the brain itself.

Chronic migraine headache constitutes yet another risk factor for thrombophilia. Migraine headache afflicts and disables millions of people yearly worldwide (Bloudek et al., *J Headache Pain* 13:361-378 (2012); Leonardi et al., *Neurol Sci* 34:S117-S118 (2013); Mauser et al., *Headache* 54:1347-1357 (2014)). Specifically, nearly 12% of the population in the United States and close to 15% of citizens of several European countries experience episodic and chronic migraine (CM) headaches, with CM (>15 headaches per month for at least 3 months) occurring in 0.9%-2.2% internationally. Migraine headache is associated with significant economic loss secondary to lost productivity and medical expenses, and in terms of years living with disability, CM is the eighth most burdensome disease, and seventh among non-communicable diseases. The precise etiologies responsible for migraine are complex and poorly defined as recently reviewed, with brainstem dysfunction and dysfunction specifically of the locus coeruleus or periaqueductal grey matter likely playing a key role (Sprenger et al., *BMC Med* 7:71 (2009)). A variety of pharmacological treatments have attenuated severity and frequency of CM, varying from oral antiepileptic administration to botulinum toxin injection—yet the mechanisms by which many of these interventions attenuate migraine are poorly understood or not explained. In sum, CM is a significant condition with marked economic impact that remains only partially mechanistically characterized and incompletely attenuated with present-day therapies.

While a mechanism clearly responsible for neuroinflammation and central pain pathway dysregulation in CM has not yet been defined, there is a constellation of clinical and laboratory findings that may point the way to a hereto unappreciated contributor to CM. First, iron appears to accumulate in deep brain nuclei associated with central pain processing (e.g., putamen, globus pallidus, red nucleus) of patients with CM (Kruit et al., *Cephalalgia* 29:351-359 (2008); Kruit et al., *Cephalalgia* 30:129-136 (2009); Tepper et al., *Headache* 52:236-243 (2012)), and patients with hereditary hemochromatosis (C282Y/C282Y genotype) have a significantly increased incidence of headache that can be attenuated by therapeutic phlebotomy (Hagen et al., *Ann Neurol* 51:786-789 (2002); Stovner et al., *Cephalalgia* 22:317-319 (2002); Gaul et al., *Headache* 47:926-928 (2007)). The mechanism by which iron modulated headache was not determined in these works (Kruit et al., *Cephalalgia* 29:351-359 (2008); Kruit et al., *Cephalalgia* 30:129-136 (2009); Tepper et al., *Headache* 52:236-243 (2012); Hagen et al., *Ann Neurol* 51:786-789 (2002); Stovner et al., *Cephalalgia* 22:317-319 (2002); Gaul et al., *Headache* 47:926-928 (2007)).

A second line of evidence concerns the relationship of obesity with CM, wherein as body mass index (BMI, kg/m$^2$) increased into the obese and morbidly obese value range, the incidence and severity of migraine also increased (Bigal et al., *Neurology* 66:545-550 (2006); Chai et al., *Headache* 54:459-471 (2014)).

Accordingly, weight loss, by either surgical or medical intervention, was associated with reduction in CM symptoms, clearly implicating obesity-mediated effects as key to CM (Novack et al., *Cephalalgia* 31:1336-1342 (2011); Verrotti et al., *Pediatr Obes* epub ahead of print (2014)). The third and last investigative line concerns the interaction of CM with coagulation. Migraineurs have over twice the risk of normal for thromboembolism, and while patent foramen ovale (PFO) may not be associated with migraine, migraineurs that have a PFO repaired are more likely to have headache relief than those that do not have repair (Schwaiger et al., *Neurology* 71:937-943 (2008); Garg et al., *Circulation* 121:1406-1412 (2010); Biasco et al., *J Cardiol* 64:390-394 (2014)).

Further, while migraineurs did not appear to have unusual hypercoagulable markers compared to headache-free controls, migraineurs administered vitamin K antagonists for conditions not related to headache improved headache symptoms, whereas patients administered clopidogrel as a prophylactic treatment did not realize significant relief from CM (Rajan et al., *Clin Appl Thromb Hemost* 20:851-856 (2014); Rahimtoola et al., *Headache* 41:768-773 (2001); Chambers et al., *Cephalalgia* 34:1163-1168 (2014)).

In sum, chronic migraineurs appear to have evidence of the involvement of iron in their pain, a contribution of obesity to their pain, and an ill-defined propensity towards plasmatic and not platelet-mediated hypercoagulability. The Hmox system, and in particular, Hmox upregulation, may be a common biochemical link between the aforementioned bodies of knowledge surrounding migraine. First, valproic acid, which has been used successfully to treat migraine, has been noted to be a Hmox inhibitor (Kwon et al., *Neurochem Int* 62:240-250 (2013)). Second, iron is a byproduct of Hmox catalysis of heme, and it enhances plasmatic coagulation via formation of carboxyhemefibrinogen (COHF) and iron-bound fibrinogen (IFIB) (Leffler et al., *Am J Physiol Heart Circ Physiol* 30: H1-H11 (2011); Nielsen et al., *Blood Coagul Fibrinolysis* 25:695-702 (2014)). Further, iron also diminishes fibrinolysis (Nielsen et al., *Blood Coagul Fibrinolysis* 25:695-702 (2014)).

Considered as a whole, as depicted in FIG. 12, it is conceivable that endogenous and exogenous CO and iron may interact with fibrinogen, enhance coagulation, modulate cerebral blood flow (e.g., microcirculatory occlusion-reperfusion) and contribute to migraine headache as either a source or amplifier of inflammatory central pain.

Given the likely importance of iron in the thrombophilic complications suffered by patients with several disease states (Kell, et al., *Metallomics*, DOI: 10.1039/c3mt00347g (2014)), it is an object of this invention to provide methods for diagnosing subjects having or suspected of having an iron-related disorder.

It is another object of the invention to provide methods for assessing the risk or likelihood that a subject has or will develop an iron-related disorder.

It is yet another object of the invention to provide methods for detecting iron-mediated plasmatic hypercoagulability and hypofibrinolysis in hemodialysis patients.

It is yet another object of the invention to provide methods for detecting iron-mediated plasmatic hypercoagulability and hypofibrinolysis in patients implanted with LVAD.

It is yet another object of the invention to provide methods for detecting iron-mediated plasmatic hypercoagulability and hypofibrinolysis in patients with Alzheimer's disease.

It is yet another object of the invention to provide methods for detecting iron-mediated plasmatic hypercoagulability and hypofibrinolysis in patients with chronic migraine.

SUMMARY OF THE INVENTION

Methods for diagnosing or assisting in the diagnosis of iron-related pathologies are provided. The methods are based on the correlation of the degree of iron-specific hypercoagulability with clinical disease. One embodiment provides a method for diagnosing or assisting in diagnosing a subject having or suspected of having an iron-related pathology by analyzing a blood sample obtained from the subject to obtain viscoelastic parameters of the blood sample as the blood sample coagulates. A variation in the viscoelastic parameters of the blood sample relative to a blood sample from a healthy subject indicates the subject has or will likely develop an iron-related pathology. Subjects having an iron-related pathology have viscoelastic parameters that are indicative of enhanced coagulation and/or diminished fibrinolysis compared to the viscoelastic parameters of the blood sample from the healthy subject.

The viscoelastic parameters to be measured include, but are not limited to one or more of CGT=clot growth time (sec), defined as the time when clot formation commences (clot strength of 102 dynes/cm$^2$ [2 mm amplitude]) to when maximum clot strength is observed; CLT=clot lysis time (sec) begins when maximum clot strength is observed and continues until lysis renders clot strength equal to 102 dynes/cm$^2$; CLS=clot lifespan (sec) is the sum of CGT and CLT; TMRTG=time to maximum rate of thrombus generation (sec); MRTG=maximum rate of thrombus generation (dynes/cm$^2$/sec); TTG=total thrombus generation (dynes/cm$^2$); TML=time to maximum rate of lysis (sec); MRL=maximum rate of lysis (-dynes/cm$^2$/sec); ACL=area under the curve of lysis (-dynes/cm$^2$), combinations thereof and subcombinations thereof.

In one embodiment, the viscoelastic parameters include one or more of time to maximum rate of thrombus generation (TMRTG); maximum rate of thrombus generation (MRTG); total thrombus generation (TTG); and clot growth time (CGT). In subjects having an iron-related pathology, one or more of the viscoelastic parameters is at least 10%, 20%, 30%, 40%, or 50% higher than the same viscoelastic parameter of a blood sample from a healthy subject. For example, at least two, at least three or at least four of the viscoelastic parameters are at least 10%, 20%, 30%, 40%, or 50% higher than the same viscoelastic parameter of a blood sample from a healthy subject.

Representative iron-related pathologies include but are not limited to biomaterial-blood interaction during mechanical circulatory support, heme-oxygenase overexpression, bacterial infection, inflammatory disorders associated with thrombophilia, hemolysis, diabetes mellitus, rheumatoid arthritis; sickle-cell anemia, thyroid cancer, breast cancer, brain cancer, thoracic cancer, colon cancer, pancreatic cancer, hemolysis, iron overload, and iatrogenic iron increases in plasmatic iron concentration.

Another embodiment provides a method for assessing the risk of a subject developing an iron-related related pathology by analyzing a blood sample from the subject to obtain viscoelastic parameters of the blood sample as the blood sample coagulates, wherein a variation, for example an increase in the viscoelastic parameters of the blood sample relative to a blood sample from a healthy subject indicates the subject has an increased risk of developing a hemolysis-related pathology.

Still another embodiment provides a method for evaluating the efficacy of a treatment for an iron-related pathology by analyzing a blood sample obtained from the subject prior to the subject receiving the treatment to obtain viscoelastic parameters of the blood sample as the blood sample coagulates. Analyzing a second blood sample obtained from the subject after the subject received the treatment to obtain viscoelastic parameters of the second blood sample as the blood sample coagulates, wherein a decrease in the viscoelastic parameters of the second blood sample taken after treatment relative to the blood sample taken prior to treatment indicates that the treatment is effective.

Still another embodiment provides a method for diagnosing or assisting in diagnosing a subject having or suspected of having thrombophilia by analyzing a blood sample from the subject to assess plasma coagulation kinetics, fibrinolytic kinetics, formation of carboxyhemefibrinogen (COHF), and upregulation of Hmox activity. A variation in the plasma coagulation kinetics, fibrinolytic kinetics, the presence of COHF in the blood sample, and the upregulation of Hmox relative to a blood sample from a healthy subject indicates that the subject has thrombophilia. In some embodiments the subject is a hemodialysis patient. In some embodiments the subject is the recipient of a left ventricular assist device (LVAD). In some embodiments the subject has Alzheimer's disease (AD). In some embodiments the subject suffers from chronic migraine.

BRIEF DESCRIPTION OF THE DRAWINGS

(FIG. 8A) 10 μl PRP were added to 5 μl FeCl$_3$ (1 mM) and mixed, followed by addition of 5 μl of thrombin; this was mixed again and incubated 3 min. Thick arrow (left)—fine fiber lattice net; *—areas of denser fibrin deposits, consisting of fine fibers (see thin arrow (right)) that are only packed closer to each other. (FIG. 8B) 10 μl of stock B CORM-2 were added to 990 μl PRP (see Table 1 for CORM-2 preparation); then 20 μl of PRP were exposed to CORM-2 followed by addition of 10 μl thrombin; this was mixed and incubated for 3 minutes. Globular fibrin packaging is visible, without typical straight fibrin fibers seen in healthy fibrin nets. Scale bar=1 μm.

DETAILED DESCRIPTION OF THE INVENTION

I. Definitions

Figure 1:
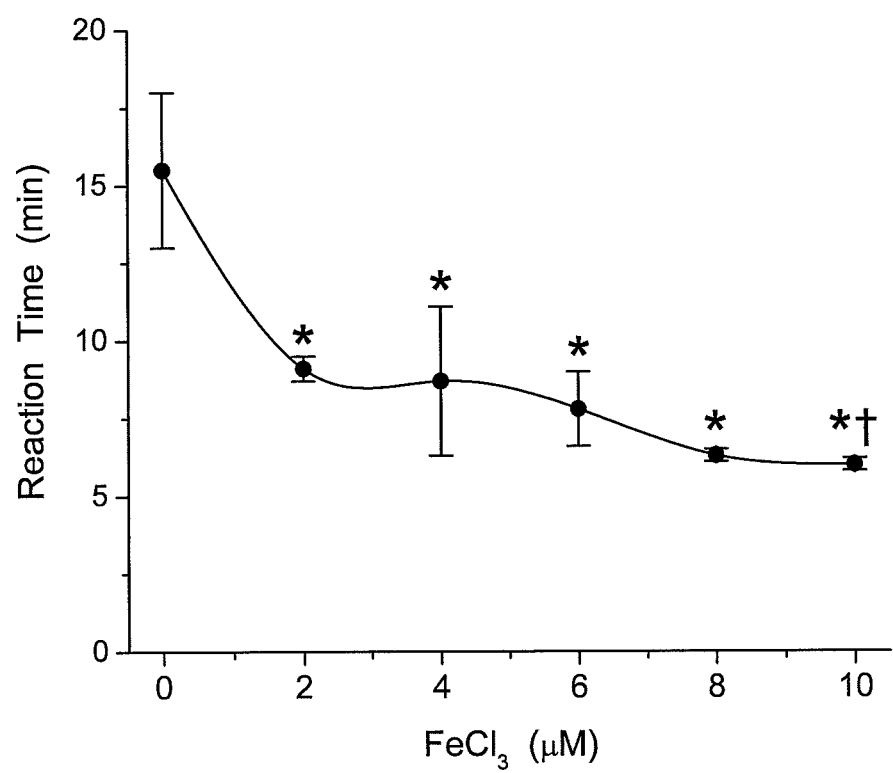
FIG. 1 is a line graph of Reaction Time (min) versus FeCl$_3$ concentration (μM) showing the effects of FeCl$_3$ concentration on reaction time in normal plasma. Data are presented as mean±SD. *p<0.05 vs. 0 μM, †P<0.05 vs. 2 μM.

The term "assay" as used herein refers to the analytic procedure for qualitatively assessing or quantitatively measuring the presence or amount or the functional activity of a target entity (the analyte).

The term "biomaterial-blood interaction during mechanical circulatory support" refers generally to the damage caused by biomaterials implanted or inserted into the subject's body. Exemplary implants include, but are not limited to stents, braces, rods, pins, heart valves, hip prosthesis, and knee replacements, joint replacements, pacemakers, artificial organs, dental implants, and cosmetic implants.

CGT=clot growth time (sec), defined as the time when clot formation commences (clot strength of 102 dynes/cm$^2$ [2 mm amplitude]) to when maximum clot strength is observed; CLT=clot lysis time (sec) begins when maximum clot strength is observed and continues until lysis renders clot strength equal to 102 dynes/cm$^2$; CLS=clot lifespan (sec) is the sum of CGT and CLT; TMRTG=time to maximum rate of thrombus generation (sec); MRTG=maximum rate of thrombus generation (dynes/cm$^2$/sec); TTG=total thrombus generation (dynes/cm$^2$); TML=time to maximum rate of lysis (sec); MRL=maximum rate of lysis (-dynes/cm$^2$/sec); ACL=area under the curve of lysis (-dynes/cm$^2$).

The term "carboxyhemefibrinogen" or "COHF" refers to the molecule that is formed when CO binds to a fibrinogen-bound heme. The formation of COHF is thought to partially mediate plasmatic hypercoagulability.

The term "chelator" as used herein refers to a binding agent that removes heavy metals from the bloodstream.

The term "coagulation" or "blood clotting" as used herein refers to the process by which blood changes from a liquid to a gel. It potentially results in hemostasis, the cessation of blood loss from a damaged vessel, followed by repair.

The term "effective" as used herein refers to being successful in producing a desired or intended result. For example, if the viscoelastic parameters from a sample of blood after the subject received treatment are 10, 20, 30, 40, or 50% lower than the viscoelastic properties of the blood sample test before treatment, the treatment is effective.

The term "fibrin" as used herein refers to a fibrous, non-globular protein involved in the clotting of blood. It is formed by the action of the protease thrombin on fibrinogen, which causes the latter to polymerize. The polymerized fibrin together with platelets forms a hemostatic plug or clot over the wound site.

The term "fibrinolysis" as used herein refers to the breakdown of a fibrin clot, which is the product of coagulation.

The term "fibrinolytic" as used herein refers to the ability of a substance to degrade fibrin and hence prevent blood clots from growing and becoming problematic.

The term "fibrinolytic kinetics" as used herein refers to the rate of fibrinolysis.

The term "heme oxygenase" or "Hmox" as used herein refers to an enzyme that catalyzes the degradation of heme, thereby producing biliverdin, iron, and CO. Accordingly, upregulation of Hmox leads to increased levels of iron and CO.

The term "hemodialysis" as used herein refers to the medical procedure that mimics the function of the kidneys by removing waste products from the blood stream.

The term "hemolysis" as used herein refers to the rupturing of red blood cells and the release of their contents into the surrounding fluid.

The term "hypofibrinolysis" as used herein refers to the reduced breakdown of fibrin clots. This state is usually associated with plasmatic hypercoagulability, leading to increased incidence of clotting.

The term "iron-related pathology" refers to diseases and disorders that are the result of or show the symptom of increased plasma concentrations for iron. Representative iron-related pathologies include, but are not limited to biomaterial-blood interaction during mechanical circulatory support, heme-oxygenase overexpression, bacterial infection, inflammatory disorders associated with thrombophilia, diabetes mellitus, rheumatoid arthritis; sickle-cell anemia, thyroid cancer, breast cancer, brain cancer, thoracic cancer, colon cancer, pancreatic cancer, hemolysis, iron overload, and iatrogenic iron increases in plasmatic iron concentration.

The term "kinetics" as used herein refers to the rate of change in a particular parameter.

The term "ventricular assist device" or "VAD" as used herein refers to an electromechanical circulatory device that is used to partially or completely replace the function of a failing heart.

The term "left ventricular assist device" or "LVAD" as used herein refers to a VAD that is designed to assist the left ventricle.

The term "plasma coagulation kinetics" as used herein refers to the rate of coagulation of blood plasma.

The term "plasmin" as used herein refers to the enzyme present in blood that degrades many blood plasma proteins, including fibrin clots.

The term "plasminogen" as used herein refers to the blood circulating glycoprotein which is the precursor of plasmin.

The term "platelets" or "thrombocytes" as used herein refers to blood cells whose function is to stop bleeding. Platelets have no nucleus, they are fragments of cytoplasm which are derived from the megakaryocytes of the bone marrow, and then enter the circulation.

The term "relative to" as used herein refers to the comparison made when a sample is measured against a control.

The term "thrombin" as used herein refers to the serine protease that converts soluble fibrinogen into insoluble strands of fibrin, and that catalyzes many other coagulation-related reactions.

The term "thrombophilia" or "plasmatic hypercoagulability" as used herein refers to an abnormality in blood coagulation that increases the risk of blood clots in blood vessels.

The term "thrombosis" as used herein refers to the formation of a blood clot inside a blood vessel that obstructs the flow of blood through the circulatory system.

The term "thrombus" or "blood clot" as used herein refers to a solid or semi-solid mass formed from the constituents of blood within the vascular system that is the product of blood coagulation. There are two components to a thrombus, aggregated platelets that form a platelet plug, and a mesh of cross-linked fibrin protein.

The term "viscoelasticity" as used herein refers to the property of materials that exhibit both viscous and elastic characteristics when undergoing deformation.

The term "viscoelastic parameters" as used herein refers to the measurable factors that define the viscoelasticity of a blood sample. These can be time to maximum rate of thrombus generation (TMRTG); maximum rate of thrombus generation (MRTG); total thrombus generation (TTG); and clot growth time (CGT).

II. Methods of Diagnosis

It has been discovered that the degree of iron specific hypercoagulability can be correlated with clinical disease, and in turn, such diagnostics can be used to assess the effectiveness of therapy targeted at diminishing circulating iron concentrations or interventions that diminish inflammatory processes that result in iron overload. Thus, one embodiment provides a method for diagnosing an iron-related pathology by assessing the efficiency of blood coagulation. The degree of iron specific hypercoagulability is then correlated with clinical disease, and in turn, such diagnostics can be used to determine whether a subject has or will develop an iron-related pathology. The diagnostics can also be used to assess the effectiveness of therapy targeted at diminishing circulating iron concentrations or interventions that diminish inflammatory processes that result in iron overload.

The data in the Examples below show that the coagulation kinetic and ultrastructural changes induced by clinically encountered free iron concentrations were partially attenuated by chelation with deferoxamine. This finding is important, as binding without generation of radical species with consequent conformational changes in fibrinogen structure can now be entertained as an important mechanism by which iron mediates hypercoagulability.

One embodiment provides using deferoxamine-mediated chelation, appropriate temperature, and sufficient incubation time, to assess the impact of iron with thrombelastography or thromboelastimetry. The role of ferritin and free iron excess in chronic diseases such as diabetes mellitus, rheumatoid arthritis, or perhaps cancer (Panis, et al., *Breast Cancer Res. Treat.*, 133:881-888 (2012)) can be assessed.

Another embodiment provides a method for diagnosing or assisting in diagnosing a subject having or suspected of having an iron-related pathology by analyzing a blood sample from the subject to obtain viscoelastic parameters of the blood sample as the blood sample coagulates. Viscoelastic parameters are measured in the absence and in the presence of an iron chelator. Suitable viscoelastic parameters include, but are not limited to CGT=clot growth time (sec), defined as the time when clot formation commences (clot strength of 102 dynes/cm$^2$ [2 mm amplitude]) to when maximum clot strength is observed; CLT=clot lysis time (sec) begins when maximum clot strength is observed and continues until lysis renders clot strength equal to 102 dynes/cm$^2$; CLS=clot lifespan (sec) is the sum of CGT and CLT; TMRTG=time to maximum rate of thrombus generation (sec); MRTG=maximum rate of thrombus generation (dynes/cm2/sec); TTG=total thrombus generation (dynes/cm$^2$); TML=time to maximum rate of lysis (sec); MRL=maximum rate of lysis (-dynes/cm$^2$/sec); ACL=area under the curve of lysis (-dynes/cm$^2$). One or more of these viscoelastic factors can be determined as well as combinations and subcombinations of these factors can be determined.

In one embodiment, time to maximum rate of thrombus generation (TMRTG); maximum rate of thrombus generation (MRTG); total thrombus generation (TTG); and clot growth time (CGT) are determined.

In another embodiment, when at least one of the viscoelastic parameters is at least 10, 20, 30, 40, or 50% higher than the same viscoelastic parameter of a blood sample from a healthy subject, the subject has or will likely develop an iron-related disorder. In still other embodiments, at least two of the viscoelastic parameters that are at least 10, 20, 30, 40, or 50% higher than the same viscoelastic parameter of a blood sample from a healthy subject is indicative of an iron-related pathology.

Representative iron-related pathologies include, but are not limited to biomaterial-blood interaction during mechanical circulatory support, heme-oxygenase overexpression, hemolysis, bacterial infection, inflammatory disorders associated with thrombophilia, diabetes mellitus, rheumatoid arthritis, sickle-cell anemia, thyroid cancer, breast cancer, brain cancer, thoracic cancer, colon cancer, pancreatic cancer, hemolysis, iron overload, iatrogenic iron increases in plasmatic iron concentration, Alzheimer's disease, and chronic migraine.

Yet another embodiment provides a method for assessing the risk of a subject developing an iron-related related pathology by analyzing a blood sample from the subject to obtain viscoelastic parameters of the blood sample as the blood sample coagulates. A variation in the viscoelastic parameters of the blood sample relative to a blood sample from a healthy subject indicates the subject has an increased risk of developing a hemolysis-related pathology. One or more viscoelastic parameters can be at least one of the viscoelastic parameters is at least 10, 20, 30, 40, or 50% higher than the same viscoelastic parameter of a blood sample from a healthy subject.

A. Thromboelastographic Methods

In one embodiment, the iron-related pathology is diagnosed using thromboelastography (TEG). TEG is a method of testing the efficiency of blood coagulation. Typically, a sample of blood is taken from a subject and rotated gently through 4° 45', six times a minute, to imitate sluggish venous flow and activate coagulation. A thin wire probe is used to measure viscoelastic parameters as the clot forms around the wire. The speed and strength of clot formation are measured in various ways, typically by computer. The speed at which the sample coagulates depends on the activity of the plasma coagulation system, platelet function, fibrinolysis and other factors that can be affected by genetics, illness, environment and medications. The patterns of changes in strength and elasticity in the clot provide information about how well the blood can perform hemostasis, and how well or poorly different factors are contributing to clot formation. This information is correlated to iron-related pathologies.

In one embodiment, four values that represent clot formation are determined by this test: the reaction time (R value), the K value, the angle and the maximum amplitude (MA). The R value represents the time until the first evidence of a clot is detected. The K value is the time from the end of R until the clot reaches 20 mm and this represents the speed of clot formation. The angle is the tangent of the curve made as the K is reached and offers similar information to K. The MA is a reflection of clot strength. A mathematical formula determined by the manufacturer can be used to determine a Coagulation Index (CI) (or overall assessment of coagulability) which takes into account the relative contribution of each of these 4 values into 1 equation.

B. Thromboelastometric Methods

In another embodiment, the viscoelastic parameters are determined using Thromboelastometery (TEM). Rotational thromboelastometry or ROTEM is a version in which the sensor shaft rotates rather than the cup. Blood (300 µl, anticoagulated with citrate) is placed into the disposable cuvette using an electronic pipette. A disposable pin is attached to a shaft that is connected with a thin spring and slowly oscillates back and forth. The signal of the pin suspended in the blood sample is transmitted via an optical detector system. The test begins by adding appropriate reagents. The instrument measures and graphically displays the changes in elasticity at all stages of the developing and resolving clot. The typical test temperature is 37° C., but different temperatures can be selected.

The primary result of TEM is a reaction curve which shows the elasticity over time when the clot forms or dissolves. This curve is also called a TEMogram.

C. Iron Chelation

In certain embodiments, the methods and assays disclosed herein assess the change in coagulation of a blood sample before and after chelation of iron in the sample. Iron chelators are known in the art. Suitable iron chelators include, but are not limited to deferoxamine (also known as desferrioxamine B, desferoxamine B, DFO-B, DFOA, DFB or DESFERAL®), deferiprone, deferasirox, desferrithiocin (DFT) [2-(3-hydroxypyridin-2-yl)-4-methyl-4,5-dihyrothiazole-4-carboxylic acid, (S)-desmethyldesferrithiocin (DMDFT), desferri-exochelin, ICL670A, CP94, tachpyridine, tachpyridine analogs, aroylhydrazones, 2-pyridylcarboxaldehyde isonicotinoyl hydrazone analogs, di-2-pyridylketone isonicotinoyl hydrazone analogs, triapine, 2-hydroxy-1-naphthylaldehyde-3-thiosemicarbazone (NT), 2-hydroxy-1-naphthaldehyde-4,4-dimethyl-3-thiosemicarbazone (N44mT), N2mT, N4mT, 2-hydroxy-1-naphthaldehyde-4-ethyl-3-thiosemicarbazone (N4eT), 2-hydroxy-1-naphthaldehyde-4-allyl-3-thiosemicarbazone (N4aT), 2-hydroxy-1-naphthaldehyde-4-phenyl-3-thiosemicarbazone (N4pT). DpT, Dp2mT, di-2-pyridylketone-4-methyl-3-thiosemicarbazone (Dp4mT), Dp44mT, di-2-pyridylketone-4-ethyl-3-thiosemicarbazone (Dp4eT), di-2-pyridylketone-4-allyl-3-thiosemicarbazone (Dp4aT), and di-2-pyridylketone-4-phenyl-3-thiosemicarbazone (Dp4pT), di-2-pyridylketone-4,4,-dimethyl-3-thiosemicarbazone (Dp44mT), and combinations thereof (see Kalinowski et al., Pharmacological Reviews 57(4):547-583 (2005) which is incorporated by reference in its entirety).

III. Methods of Evaluating Treatment

The methods for measuring the viscoelastic properties of clot formation can be used to assess the effectiveness of a treatment for iron-related pathology. For example, viscoelastic properties of clot formation can be determined using thromboelastographic or thromboelastometric methods described above. A sample of blood from a subject can be assayed before and after the subject receives a treatment for an iron-related pathology. If the viscoelastic parameters from the sample of blood after the subject received treatment are 10, 20, 30, 40, or 50% lower than the viscoelastic properties of the blood sample test before treatment, the treatment is effective. Similarly, if the viscoelastic properties of the blood sample assayed after the subject received the treatment are unchanged or higher that the parameters of the sample assayed prior to treatment, the treatment is not effective.

IV. Iron-Related Pathologies

The correlation of iron-specific hypercoagulability with iron-related pathologies enables the diagnosis of iron-related pathologies by assessing the degree of hypercoagulability in a blood sample from a subject using the disclosed methods. By determining the viscoelastic parameters of a sample of blood as the blood clots, one can diagnose or assist in the diagnosis of specific diseases. These diseases include but are not limited to biomaterial-blood interaction during mechanical circulatory support, heme-oxygenase overexpression, hemolysis, bacterial infection, inflammatory disorders associated with thrombophilia, diabetes mellitus, rheumatoid arthritis, sickle-cell anemia, thyroid cancer, breast cancer, brain cancer, thoracic cancer, colon cancer, pancreatic cancer, hemolysis, iron overload, and iatrogenic iron increases in plasmatic iron concentration.

Biomaterial-blood interactions include interactions between implants and other materials inserted into a subject. For example, stents and prosthetics can cause blood cell lysis leading to increased levels of iron in the serum which leads to iron specific hypercoagulation. By assessing iron-specific hypercoagulation in a subject inserted with a biomaterial, one can determine whether the biomaterial is causing or contributing to hypercoagulation. The subject can then be treated accordingly. Exemplary biomaterial-blood interactions occur with prosthetic heart valves which can cause or contribute to hemolysis and hypercoagulation.

Similarly, other pathologies that show increased concentrations of serum iron or iron-specific hypercoagulation can be detected or diagnosed using the disclosed methods. The diagnosis can be confirmed or supported by using a second test for the pathology.

EXAMPLES

Example 1

Effects of $FeCl_3$ and Deferoxamine on Reaction Time

Methods

Thrombelastograph-Based Analyses. All thrombelastograph-based experiments were performed at the University of Arizona. Frozen, citrate anticoagulated normal pooled plasma was obtained from a commercial vendor (George King Bio-Medical, Overland Park, Kans., USA) for use in subsequently described experimentation. With regard to chemicals utilized, ferric chloride ($FeCl_3$, 99.9% pure) and calcium-free phosphate buffered saline (PBS) were obtained from a commercial vendor (Sigma-Aldrich, Saint Louis, Mo., USA). Deferoxamine was obtained from a commercial vendor (Cayman Chemical Company, Ann Arbor, Mich., USA).

First, a concentration-response relationship of iron concentration and reaction time (R, defined as 2 mm clot strength; this is also known as clotting time in thromboelastometric analyses) was determined. The rationale for using R time was that it is the first indication of the onset of coagulation, is used in both thrombelastographic and thromboelastometric systems, and was anticipated to quickly and easily detect iron-mediated enhancement of coagulation based on previous work. This concentration-response relationship was generated with a ROTEM® delta hemostasis system (Tem Innovations GmbH, Munich, Germany) generously provided by the manufacturer. All disposable cups/pins and reagents were also provided by Tem Innovations. Plasma was rapidly thawed at 37° C. on the day of experimentation. Separate aliquots of plasma were exposed to 1% v/v additions of ferric chloride dissolved in PBS that resulted in final concentrations of 0, 2, 4, 6, 8 or 10 µM (n=5-6 replicates per concentration). After 3 min or more of incubation at room temperature, 320 µl of these iron-exposed plasmas were subsequently placed in a disposable cup, with subsequent addition of 20 µl of 200 mM $CaCl_2$. The complete sample was mixed by pipette once, and the reaction commenced at 37° C. The R values were subsequently recorded.

The second series of experiments examined the role of time on chelation of iron from plasma and consequent changes in R. First, plasma that was rapidly thawed at 37° C. on the day of experimentation was exposed to either a 1% v/v addition of PBS or $FeCl_3$ (10 µM final concentration) for 3 min. Then, 336 µl of either plasma mixture was placed in a disposable cup in a computer-controlled thrombelastograph® hemostasis system (Model 5000, Haemoscope Corp., Niles, Ill., USA). An addition of 3.6 µl deferoxamine in $dH_2O$ (0 or 1 mM final concentration) was added to the plasma mixture, mixed with the disposable pin, and allowed to incubate for 3 min at 37° C. Thus, there were four conditions: no deferoxamine, no $FeCl_3$, (Control), deferoxamine, no $FeCl_3$ (deferoxamine); no deferoxamine, $FeCl_3$ ($FeCl_3$); and finally, $FeCl_3$ followed by deferoxamine ($FeCl_3$+Deferoxamine). There were six replicates per condition. Thereafter, 20 µl of 200 mM $CaCl_2$ was added as the last step to initiate clotting. Data were collected at 37° C. until R was recorded. In the next set of this experimental series, an identical addition of PBS or $FeCl_3$ to plasma was performed with a 3 min incubation, followed by a 1% v/v of deferoxamine (0 or 1 mM final concentration), with this plasma kept in a sealed tube at room temperature for approximately 40 min. There were six replicates per condition. An aliquot of 340 µl of each of the four conditions was placed into thrombelastographic cups and 20 µl of 200 mM $CaCl_2$ was added to initiate clotting. Data were collected at 37° C. until R was recorded. As R values varied between experiments, and a fixed number of channels were available (n=4), plasma was incubated at room temperature between 45-60 min prior to initiation of coagulation.

The third series of experiments was designed to decrease incubation time by increasing temperature and deferoxamine concentration without compromising the ability to detect iron-mediated changes in R values. In these experiments, plasma had a 1% v/v addition of PBS or $FeCl_3$ (10 µM final concentration) followed by a 3 min incubation at room temperature. Subsequently 330 µl of either of these plasma types were placed in disposable thrombelastograph cups, with addition of 10 µl of $dH_2O$ or 100 mM deferoxamine (2.78 mM final concentration). The mixtures were mixed with the disposable pin, and allowed to incubate for 15 min at 37° C. Clotting was initiated by addition of 20 μl of 200mM CaCl$_2$ and data collected at 37° C. until R was recorded. A total of six replicates of the four experimental conditions were analyzed.

SEM-Based Analyses. All SEM-based analyses were conducted at the University of Pretoria. For the SEM experiments, eighty ml of whole blood was collected from a single donor, and anticoagulated with sodium citrate (9 parts blood to 1 part 0.105M sodium citrate), and platelet rich plasma (PRP) was obtained from each collected sample by centrifuging the whole blood at 1250×g for 2 min. The donor was a healthy, non-smoking female individual (age: 45; serum ferritin level: 13 ng/ml and percentage of iron saturation: 22%). In the SEM experiments, 6 different combinations of products and incubation times were prepared (C1 to C6). For the experimental procedures, see Table 2.

SEM preparation involved a washing of C1 to C6 in 0.075 M PBS for 20 minutes to remove any plasma and product residues, followed by fixing in 4% formaldehyde for 30 minutes, followed by three washing steps in 0.075 M PBS for three minutes to remove any residual fixative. The smears were then post-fixated for 15 minutes with 1% osmium tetroxide (OsO4), followed by a washing process, for three minutes in 0.075M PBS. The samples were finally dehydrated serially in 30%, 50%, 70%, 90% and then three times in 100% ethanol followed by drying using hexamethyldisilazane; mounting and coating with carbon. Once the samples had been coated they were examined using a scanning electron microscope (Zeiss ULTRA plus FEG SEM, Carl Zeiss Microscopy GmbH, Jena, Germany). The Institutional Review Board of the University of Pretoria granted approval for healthy individuals for SEM-based investigations (ethics number 151/2006 (E Pretorius) that is extended until end of 2014).

Statistical Analyses and Graphics. R data are presented as mean±SD, with analyses conducted with a commercially available statistical program (SigmaStat 3.1, Systat Software, Inc., San Jose, Calif., USA). Graphics were generated with a commercially available program (OrigenPro 7.5, OrigenLab Corporation, Northampton, Mass., USA). The analysis of the effects of increasing the concentration of FeCl$_3$ on R values was conducted with one-way analysis of variance with the Holm-Sidak post hoc test. As the subsequent data generated in thrombelastographic experiments violated assumptions of normality and variance, these analyses of the effects of FeCl$_3$ and deferoxamine on R values were conducted with Kruskal-Wallis one-way analysis of variance with the Student-Newman-Keuls post hoc test. A P value of <0.05 was considered significant. Micrographs of SEM data were generated with Adobe Photoshop CS6 (Adobe Systems Inc., San Jose, Calif., USA).

Results

Thrombelastographic Data. Data from the various series of experiments are displayed in FIG. 1 and Table 2. As seen in FIG. 1, the addition of 2-10 μM FeCl$_3$ to plasma resulted in R values significantly smaller than plasma without FeCl$_3$ addition. Only samples exposed to 10 μM FeCl$_3$ had R values significantly smaller than those exposed to 2 μM FeCl$_3$. The degree of reduction in R values by addition of FeCl$_3$ varied by 39% to 61% of values observed in samples not exposed to FeCl$_3$.

The results concerning the effects of chelation on R values are depicted in Table 2. Exposure to deferoxamine for 3 min resulted in a small but significant decrease in R values compared to control plasma values. Exposure to FeCl$_3$ resulted in a significant, 54% reduction in R values compared to control plasma values. This significant, FeCl$_3$-mediated decrease in R values did not significantly change when deferoxamine was added for an additional 3 min incubation. However, after a 45-60 minute incubation, the significant, FeCl$_3$-mediated (72%) decrease in R values was significantly attenuated by addition of deferoxamine. Compared to samples with FeCl$_3$ addition alone, samples incubated with deferoxamine for 45-60 min after FeCl$_3$ addition had a 108% increase in R values. This pattern of successful chelation of iron by deferoxamine and partial restoration of R values towards that of control plasma was observed in plasma incubated at 37° C. for 15 min following addition of 2.78 mM deferoxamine.

TABLE 2

Effects of FeCl$_3$ and deferoxamine on reaction time (min).

| Control | Deferoxamine | FeCl$_3$ | FeCl$_3$ + Deferoxamine |
|---|---|---|---|
| Three Min Incubation at Room Temperature, Deferoxamine 1 mM | | | |
| 13.4 (12.7, 14.4) | 11.6 (11.2, 12.1)* | 5.9 (5.8, 6.4)*† | 6.2 (4.9, 6.3)*† |
| Forty-Five to Sixty Min Incubation at Room Temperature, Deferoxamine 1 mM | | | |
| 17.9 (15.2, 20.4) | 17.4 (16.2, 18.6) | 5.0 (4.9, 5.1)*† | 10.4 (9.5, 11.0)*†‡ |
| Fifteen Min Incubation at 37° C., Deferoxamine 2.78 mM | | | |
| 18.8 (14.0, 29.1) | 16.2 (13.1, 19.7) | 4.6 (4.4, 6.0)*† | 9.2 (9.0, 9.4)*†‡ |

FeCl$_3$ final concentration was 10 μM in all conditions where present. Data presented as median (1$^{st}$, 3$^{rd}$ quartile).
*P < 0.05 vs. Control,
†P < 0.05 vs. Deferoxamine,
‡P < 0.05 vs. FeCl$_3$.

Example 2

Role of Iron in Coagulation

Methods

Normal Individual and Hemodialysis Patient Plasma

Normal Individual Plasma

Normal individual plasma obtained (George King Bio-Medical, Overland Park, Kans.) anticoagulated with sodium citrate (9 parts blood to 1 part 0.105M sodium citrate during processing) was used for experimentation. A standard lot of 30 patients (15 males, 15 females; mean age 30 years, with range of 20-47 years) were used. All normal subjects were verified to be without bloodborne disease (e.g., hepatitis), not pregnant, and nonsmokers as per the vendor's specifications. The rationale for using plasma of this nature is that standard, plasma-based tests of coagulation (e.g., prothrombin time, activated prothrombin time, fibrinogen concentration, and coagulation factor activities) commonly have 95% confidence interval (CI) values in clinical pathology laboratories within hospitals/ambulatory clinics established with such material. Indeed, that is the express commercial purpose of the manufacturing of such normal subject plasma lots, as most facilities do not have the resources or time to insure that their normal reference population is actually disease/medication-free. Furthermore, by using the same lot of plasma for reference between hospitals, a greater standardization of "normality" is realized, so that comparison of patient population sample values across institutions is more reasonable. As multi-institutional comparisons with the subsequently described thrombelastograph-based assays were anticipated, it was prudent to use standardized, normal subject plasma obtained from an internationally recognized commercial vendor.

Hemodialysis Patients

The protocol (13-0532) was approved by the University of Arizona Institutional Review Board (IRB). Furthermore, the protocol with IRB approval was reviewed and approved by Dialysis Clinic, Inc. (DCI; approval #2013.34), the corporate offices of which are in Nashville, Tenn. As the University of Arizona does not provide chronic dialysis services, the assistance of DCI facilities in the Tucson area was obtained to recruit patients; these facilities have medical oversight from nephrologists that included two of the authors of this work (A.N.S. and M.M.). Patients undergoing chronic hemodialysis, aged 18-80, and not being administered heparinoids chronically, were recruited for this investigation. The patients had no history of inherited bleeding disorder, and tobacco smokers and patients receiving warfarin were also recruited. After written consent was obtained, the concentration of COHb present was recorded via noninvasive pulse oximetry (Model Rad57, Masimo Corporation, Irvine, Calif. Accuracy is ±1% as per the manufacturer). Then, after hemodialysis access was obtained via arteriovenous fistula or vascular catheter, but before the administration of heparin and commencement of hemodialysis, a sample of whole blood (5 ml) was obtained from the patients. This blood sample was anticoagulated with sodium citrate (9 parts blood to 1 part 0.105M sodium citrate) and subsequently centrifuged at 3000 g for 15 min at room temperature, with plasma decanted, aliquoted and immediately frozen on dry ice at the DCI facility. The samples were subsequently transported back to the University of Arizona and stored at −80° C. before experimentation.

Thromboelastographic Analyses

Fibrinolytic Kinetic Analyses

Plasma was rapidly thawed at 37° C. on the day of experimentation. The final volume for all subsequently described plasma sample mixtures was 360 µl. Sample composition consisted of 320 µl of plasma; 10 µl of tissue factor reagent (0.1% final concentration in $dH_2O$; Diagnostica Stago S.A.S., Asnieres sur Seine, France), 10 µl of tissue type plasminogen activator (580 IU/µg, Genentech, Inc., San Francisco, Calif.; 100 IU/ml final concentration), and 20 µl of 200 mM $CaCl_2$ as described previously (Arkebauer et al., *Blood Coagul Fibrinolysis* 22:712-719 (2011); Nielsen et al., *Blood Coagul Fibrinolysis* 23:104-107 (2012)). Plasma sample mixtures were placed in a disposable cup in a computer-controlled thrombelastograph hemostasis system (Model 5000, Haemoscope Corp., Niles, Ill.), with addition of $CaCl_2$ as the last step to initiate clotting. Data were collected at 37° C. until clot lysis time (CLT) was observed. Elastic modulus-based parameters of fibrinolysis recorded included time to maximum rate of lysis (TMRL, min), maximum rate of lysis (MRL, dynes/cm2/sec) and CLT as previously described (Arkebauer et al., *Blood Coagul Fibrinolysis* 22:712-719 (2011); Nielsen et al., *Blood Coagul Fibrinolysis* 23:104-107 (2012)).

Iron-Enhanced Coagulation Detection Assay

In initial review, there was some question if COHb and COHF measured in hemodialysis patients originated from endogenous Hmox activity upregulation. To address this concern and further document upregulation of Hmox, residual citrated plasma that remained in sufficient quantity to perform the subsequently described assay was identified from 35 of our patients. Free iron is a product of Hmox activity (Balla et al., *Antioxid Redox Signal* 9:2119-2137 (2007)), and enhancement of fibrinogen as a substrate by iron was recently described (Nielsen et al., *Blood Coagul Fibrinolysis* 25:695-702 (2014)) and have devised a method to thrombelastographically assess iron presence (Nielsen et al., *Blood Coagul Fibrinolysis* 25:845-850 (2014)). In brief, the samples consisted of 320 µl of plasma, 20 µl $dH_2O$ or deferoxamine (5.6 mM final concentration; Sigma-Aldrich) that were incubated for 15 min at 37° C. in the thrombelastograph cups, before addition of 20 µl of 200 mM $CaCl_2$, a modification of our previously described assay (Nielsen et al., *Blood Coagul Fibrinolysis* 25:845-850 (2014)). Data were collected until the angle of the sample was determined, with comparison of the MRTG the primary determinant of iron-mediated enhancement of coagulation as previously described (Nielsen et al., *Blood Coagul Fibrinolysis* 25:695-702 (2014)). The normal, nonspecific amount of decrease in MRTG secondary to deferoxamine exposure was defined by the differences in the means between 10 replicates of the two conditions (without and with deferoxamine) in pooled normal plasma (George King Bio-Medical, Overland Park, Kans.) plus two standard deviations of the deferoxamine-exposed replicates—this amounted to a decrease of 1.2 dynes/cm2/sec. Thus, a decrease in MRTG>1.2 dynes/cm2/sec after deferoxamine exposure would define the presence of iron-mediated enhancement of coagulation (upper limit of normal; lower limit of normal was <−0.8 dynes/cm2/sec).

Statistical Analyses and Graphics

Data are presented as mean±SD, individual parameter values, % incidence with 95% CI, or simply 95% CI depending on the table or figure format. One comparison utilized Student's t-test. A commercially available statistical program was used for these analyses (SigmaStat 3.1, Systat Software, Inc., San Jose, Calif.). Confidence interval was determined for % incidence with the Clopper-Pearson method. Coagulation kinetic and fibrinolysis kinetic parameters of hemodialysis patient samples were compared with 95% CIs generated from normal subject plasma. Graphics were generated with a commercially available program (OrigenPro 7.5, OrigenLab Corporation, Northampton, Mass.; CorelDRAW12, Corel Corporation, Mountain View, Calif.).

Results

Fifty hemodialysis patients were recruited; however, 5 blood samples were mishandled and could not be analyzed. Thus, a complete dataset for 45 hemodialysis patients was obtained. The age of these patients was 56±16 years, with a male:female ratio of 21:24. The COHb concentration of our patients was 2.2±1.9% (range 0%-6.7%), well above the 0.9% threshold for increased cardiovascular morbidity (Hedblad et al., *Scand J Public Health* 34:609-615 (2006)). Nonsmokers had a COHb concentration of 2.0±1.6%, which was significantly ($p<0.005$ by one tail t-test) less than that of the 5 smokers, which was 4.3±2.5%. With regard to comorbid conditions, warfarin administration and tobacco smoking, these data are displayed in Table 3.

TABLE 3

Clinical Characteristics of Hemodialysis Patients

| | Incidence % (n) |
|---|---|
| History of Atherosclerosis or Thrombosis | |
| Any | 38 (17) |
| Coronary artery disease | 31 (14) |
| Myocardial infarction | 13 (6) |
| Cerebral vascular events | 7 (3) |
| Deep venous thrombosis | 2 (1) |
| Renal-related medical history | |
| Hypertension | 84 (38) |
| Diabetes mellitus type 1 | 4 (2) |
| Diabetes mellitus type 2 | 53 (24) |
| Glomerulonephritis | 7 (3) |
| Systemic lupus erythematosus | 4 (2) |
| Wegner's granulomatosis | 2 (1) |
| Anemia | 67 (30) |
| Other cardiovascular disease | |
| Congestive heart failure | 16 (7) |
| Atrial fibrillation | 2 (1) |
| Peripheral vascular disease | 7 (3) |
| Miscellaneous | |
| Tobacco smoking | 11 (5) |
| Warfarin administration | 9 (4) |
| Erythropoietin administration | 7 (3) |

With regard to normal individual plasma values, the 95% CI values for coagulation and fibrinolytic kinetic parameters are displayed in Table 4. The normal individual FRG (based on individual, not group mean responses) was 123%. Thus, for a hemodialysis patient to be considered hypercoagulable or hypofibrinolytic, the coagulation kinetic parameter value of interest had to be outside the normal 95% CI values; similarly, for COHF to be considered present, the FRG value had to be less than 123%.

TABLE 4

Normal 95% CI Values for Coagulation
and Fibrinolytic Kinetic Parameters

| Parameter | Values |
|---|---|
| TMRTG (min) | 2.6-4.3 |
| MRTG (dynes/cm2/sec) | 3.8-8.9 |
| TTG (dynes/cm2) | 127-237 |
| TMRL (min) | 3.6-24.9 |
| MRL (dynes/cm2/sec) | 0.6-1.4 |
| MRL (dynes/cm2/sec) | 13.0-34.5 |

CI, confidence interval; CLT, clot lysis time; MRL, maximum rate of lysis; MRTG, maximum rate of thrombus generation; TMRL, time to maximum rate of lysis; TMRTG, time to maximum rate of thrombus generation; TTG, total thrombus generation.

Figure 2:
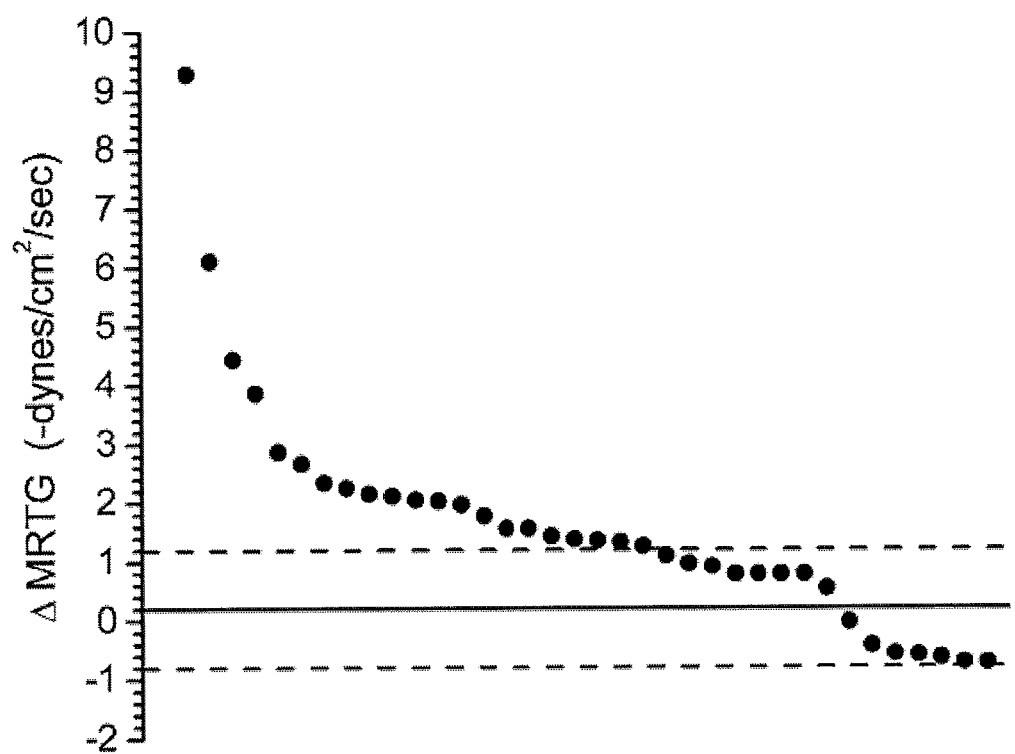
FIG. 2 is a scatter dot graph showing iron-mediated enhancement of MRTG in hemodialysis patient plasma. Individual data are represented by each circle. Dashed lines represent the upper and lower limits of normal derived from pooled normal plasma as described in the text. MRTG, maximum rate of thrombus generation.

FIG. 2 displays the degree by which deferoxamine diminished MRTG in residual plasma obtained from 35 patients. Twenty-one of the 35 had MRTG values decreased beyond the upper limits of normal, accounting for 60% (42.1%-76.1%) of this subset of patients, indicative of iron enhancement of coagulation.

Example 3

Role of Iron in Plasmatic Hypercoagulability and Hypofibrinolysis in Patients Implanted with LVAD for One Month or Greater Methods Normal Individual and LVAD Patient Plasma Normal Individual Plasma Normal individual plasma obtained (George King BioMedical, Overland Park, Kans., USA) anticoagulated with sodium citrate (9 parts blood to 1 part 0.105M sodium citrate during processing) was utilized for experimentation. A standard lot of 30 individuals (15 males, 15 females; mean age 30 years, with range of 20 years to 47 years) were utilized. All normal subjects were verified to be without blood borne disease (e.g., hepatitis), not pregnant, and nonsmokers as per the vendor's specifications. The rationale for using plasma of this nature is that standard, plasma-based tests of coagulation (e.g., prothrombin time, activated prothrombin time, fibrinogen concentration, and coagulation factor activities) commonly have 95% confidence interval values in clinical pathology laboratories within hospitals/ambulatory clinics established with such material. Indeed, that is the express commercial purpose of the manufacturing of such normal subject plasma lots, as most facilities do not have the resources or time to insure that their normal reference population is actually disease/medication free. Further, by using the same lot of plasma for reference between hospitals, a greater standardization of "normality" is realized, so that comparison of patient population sample values across institutions is more reasonable. As multi-institutional comparisons with the subsequently described thrombelastograph-based assays, it was prudent to use standardized, normal subject plasma obtained from an internationally recognized commercial vendor.

LVAD Patient Plasma

The protocol was approved by the University of Louisville Institutional Review Board and consent was obtained prior to LVAD implantation. Patients implanted with either the HMII or HVAD for a month or longer, aged 18 years of age and older, and not being administered heparinoids chronically, were included in this investigation. The LVAD outflow graft implanted in all patients had the anastomosis slightly beveled at 45° degrees on the greater curvature of the ascending aorta pointing towards the arch. The patients had no history of inherited bleeding disorder, and patients could not be tobacco smokers as this would enhance coagulation as previously noted (Nielsen et al., *Blood Coagul Fibrinolysis* 24:405-410 (2013)). After written consent was obtained, a sample of whole blood (15 ml) was obtained from the patients. This blood sample was anticoagulated with sodium citrate (9 parts blood to 1 part 0.105M sodium citrate) and subsequently centrifuged at 3000×g for 15 min at room temperature, with plasma decanted, aliquoted and immediately frozen at −80° C. and stored at the University of Louisville. The samples were subsequently transported on dry ice to the University of Arizona and stored at −80° C. prior to experimentation. Lastly, medical and surgical patient data were collected for correlation with laboratory findings.

Thrombelastographic Analyses

All of the following laboratory analyses were personally conducted by a clinician scientist who was blinded to all clinical parameters of the LVAD patients studied prior to completion of experimentation and analysis of hemostatic data.

Coagulation Kinetic Analyses and COHF Assay

Plasma was rapidly thawed at 37° C. on the day of experimentation. The final volume for all subsequently described plasma sample mixtures was 359.4 μl. Sample composition consisted of 326 μl of plasma; 10 μl of tissue factor reagent (0.1% final concentration in distilled water; Diagnostica Stago S.A.S., Asnieres sur Seine, France), 3.6 μl of distilled water or CORM-2 (carbon monoxide releasing molecule-2; tricarbonyldichlororuthenium (II) dimer, 100 μM final concentration; Sigma-Aldrich, Saint Louis, Mo., USA) and 20 μl of 200 mM $CaCl_2$ as per our previously described COHF assay (Nielsen et al., *Blood Coagul Fibrinolysis* 24:405-410 (2013); Matika et al., *ASAIO J* 60:716-721 (2014); Thompson et al., *J Thromb Thrombolysis* epub ahead of print (2014)). This concentration of CORM-2 reliably increases clot strength in the absence of CO (Nielsen et al., *Blood Coagul Fibrinolysis* 24:405-410 (2013); Matika et al., *ASAIO J* 60:716-721 (2014); Thompson et al., *J Thromb Thrombolysis* epub ahead of print (2014)). Plasma sample mixtures were placed in a disposable cup in a computer-controlled thrombelastograph® hemostasis system (Model 5000, Haemoscope Corp., Niles, Ill., USA), with addition of $CaCl_2$ as the last step to initiate clotting. Data were collected at 37° C. for 15 min. The following elastic modulus-based parameters previously described (Benk et al., *Eur J Cardio-Thorac Surg* 44:551-558 (2013); Owens *Clin Biochem* 43:1183-1188 (2010); Balla et al., *Antioxid Redox Signal* 9:2119-2137 (2007); Nielsen et al., *Blood Coagul Fibrinolysis* 20:377-380 (2009); Nielsen et al., *Blood Coagul Fibrinolysis* 22:443-447 (2011); Nielsen et al., *Blood Coagul Fibrinolysis* 22:756-759 (2011); Nielsen et al., *Blood Coagul Fibrinolysis* 24:405-410 (2013)) were determined: time to maximum rate of thrombus generation (TMRTG): this is the time interval (min) observed prior to maximum speed of clot growth; maximum rate of thrombus generation (MRTG): this is the maximum velocity of clot growth observed (dynes/$cm^2$/sec); and total thrombus generation (TTG, dynes/$cm^2$), the final viscoelastic resistance observed after clot formation.

Using this method, hypercoagulability was subsequently described as a TTG value >95% confidence interval value of the normal subjects data set. Modifying our previous definition of COHF formation, the presence of COHF was defined as a sum of the % increase in TTG secondary to CORM-2 exposure that was significantly less than the average value of similar measurements in normal subject samples.

Iron-Enhanced Coagulation Detection Assay

Plasma samples consisted of 320 μl of plasma, 20 μl $dH_2O$ or deferoxamine (5.6 mM final concentration; Sigma-Aldrich, Saint Louis, Mo., USA) that were incubated for 15 min at 37° C. in the thrombelastograph cups, prior to addition of 20 μl of 200 mM $CaCl_2$ (Matika et al., *ASAIO J* 60:716-721 (2014); Thompson et al., *J Thromb Thrombolysis* epub ahead of print (2014); Nielsen et al., *Blood Coagul Fibrinolysis* 25:845-850 (2014)). Data were collected until the angle of the sample was determined, with comparison of the MRTG the primary determinant of iron-mediated enhancement of coagulation as previously described (Matika et al., *ASAIO J* 60:716-721 (2014); Thompson et al., *J Thromb Thrombolysis* epub ahead of print (2014)). The normal, nonspecific amount of decrease in MRTG secondary to deferoxamine exposure was defined by the differences in the means between ten replicates of the two conditions (without and with deferoxamine) in pooled normal plasma (George King Bio-Medical, Overland Park, Kans., USA) plus two standard deviations of the deferoxamine exposed replicates—this amounted to a decrease of 1.2 dynes/$cm^2$/sec. Thus, a decrease in MRTG>1.2 dynes/$cm^2$/sec after deferoxamine exposure would define the presence of iron-mediated enhancement of coagulation (upper limit of normal; lower limit of normal was <-0.8 dynes/$cm^2$/sec).

Fibrinolytic Kinetic Analyses

Plasma was rapidly thawed at 37° C. on the day of experimentation. The final volume for all subsequently described plasma sample mixtures was 360 μl. Sample composition consisted of 320 μl of plasma; 10 μl of tissue factor reagent (0.1% final concentration in $dH_2O$; Diagnostica Stago S.A.S., Asnieres sur Seine, France), 10 μl of tissue type plasminogen activator (tPA, 580 IU/μg, Genentech, Inc., San Francisco, Calif., USA; 100 IU/ml final concentration), and 20 μl of 200 mM $CaCl_2$ as described previously (Arkebauer et al., *Blood Coagul Fibrinolysis* 22:712-719 (2011); Nielsen et al., *Blood Coagul Fibrinolysis* 23:104-107 (2012); Nielsen et al., *Blood Coagul Fibrinolysis* 25:695-702 (2014); Matika et al., *ASAIO J* 60:716-721 (2014); Thompson et al., *J Thromb Thrombolysis* epub ahead of print (2014)). Plasma sample mixtures were placed in a disposable cup in a computer-controlled thrombelastograph hemostasis system (Model 5000, Haemoscope Corp., Niles, Ill., USA), with addition of $CaCl_2$ as the last step to initiate clotting. Data were collected at 37° C. until clot lysis time (CLT) was observed. Elastic modulus-based parameters of fibrinolysis recorded included time to maximum rate of lysis (TMRL, min), maximum rate of lysis (MRL, dynes/$cm^2$/sec) and CLT as previously described (Arkebauer et al., *Blood Coagul Fibrinolysis* 22:712-719 (2011); Nielsen et al., *Blood Coagul Fibrinolysis* 23:104-107 (2012); Nielsen et al., *Blood Coagul Fibrinolysis* 25:695-702 (2014); Matika et al., *ASAIO J* 60:716-721 (2014); Thompson et al., *J Thromb Thrombolysis* epub ahead of print (2014)).

Statistical Analyses and Graphics

These data are presented as mean±SD with range, individual parameter values, and % incidence with normal subject 95% confidence. intervals (CI) depending on the table or figure format. A commercially available statistical program was used for these analyses (SigmaStat 3.1, Systat Software, Inc., San Jose, Calif., USA). CI was determined for % incidence with the Clopper-Pearson method. Coagulation kinetic and fibrinolysis kinetic parameters of hemodialysis patient samples were compared with 95% confidence intervals generated from normal subject plasma. Graphics were generated with a commercially available program (OrigenPro 7.5, OrigenLab Corporation, Northampton, Mass., USA; CorelDRAW12, Corel Corporation, Mountain View, Calif., USA).

Results

Sixteen LVAD patients that were not tobacco smokers were recruited; all were male, and the age of these patients was 54±16 (range 18-81) years. Exclusion of tobacco smokers diminished habitual exposure to CO released during combustion, which would be expected to affect the aforementioned thrombelastographic analyses (Nielsen et al., *Blood Coagul Fibrinolysis* 24:405-410 (2013)). The body mass index (BMI, kg/$m^2$) of this group was 29±9 (19-59). Table 5 lists the patient comorbid conditions, device used, and reason for implantation. Table 6 lists patient clinical laboratory values obtained during routine clinical surveillance at the time blood was collected for the present investigation. It is particularly noteworthy that the circulating LDH values of these patients were on average smaller than those displayed in Table 4, indicative of a small amount of device-mediated hemolysis. With regard to anticoagulation, patients were administered warfarin 1.0-7.5 mg per day to achieve an international normalized ratio value of 2.5±0.5, and aspirin 81-325 mg per day was administered as antiplatelet therapy. At the time of blood sample collection, the patients had been implanted with their device for 13±16 (1-47) months.

TABLE 5

Clinical characteristics of LVAD patients.

|  | Incidence (% and (number) of patients) |
|---|---|
| Medical Conditions |  |
| Ischemic Cardiomyopathy | 69% (11) |
| Idiopathic Cardiomyopathy | 31% (5) |
| Diabetes Mellitus (Type 1 or 2) | 25% (4) |
| Obesity (BMI >30 kg/m$^2$) | 25% (4) |
| Obstructive Sleep Apnea | 25% (4) |
| VAD-Related Data |  |
| HM II | 69% (11) |
| HVAD | 31% (5) |
| Bridge to Transplantation | 38% (6) |
| Destination Therapy | 62% (10) |

TABLE 6

Laboratory parameter values of LVAD patients.

| Parameter | Values (mean ± SD, (range)) |
|---|---|
| Serum Albumin (g/dL) | 3.6 ± 0.3 (3.0-4.1) |
| Hemoglobin (g/dL) | 13.0 ± +1.7 (8.1-15.3) |
| Hematocrit (%) | 38.9 ± +5.2 (24.5-46.4) |
| LDH (U/L) | 212 ± 36 (147-263) |
| INR | 1.8 ± 0.7 (1.0-3.3) |
| Fibrinogen (mg/dL) | 333 ± 77 (232-495) |
| Platelets (10$^9$/L) | 225 ± 95 (97-438) |

LDH = lactate dehydrogenase; INR = international normalized ratio.

With regard to normal individual plasma values, the 95% confidence interval values for coagulation and fibrinolytic kinetic parameters are displayed in Table 7. The normal individual increase in TTG secondary to CORM-2 exposure (based on individual, not group mean responses) was 89%. Thus, for an LVAD patient to be considered hypercoagulable or hypofibrinolytic, the coagulation kinetic parameter value of interest had to be outside the normal 95% CI values; similarly, for COHF to be considered present, the increase in TTG value had to be less than 89%.

TABLE 7

Normal 95% CI values for coagulation and fibrinolytic kinetic parameters.

| Parameter | Values |
|---|---|
| TMRTG (min) | 2.6-4.3 |
| MRTG (dynes/cm$^2$/sec) | 3.8-8.9 |
| TTG (dynes/cm$^2$) | 127-237 |
| TMRL (min) | 3.6-24.9 |
| MRL (dynes/cm$^2$/sec) | 0.6-1.4 |
| CLT (min) | 13.0-34.5 |

Time to maximum rate of thrombus generation (TMRTG): this is the time interval (min) observed prior to maximum speed of clot growth; Maximum rate of thrombus generation (MRTG): this is the maximum velocity of clot growth observed (dynes/cm$^2$/sec); Total thrombus generation (TTG): this is the total area under the velocity curve during clot growth (dynes/cm$^2$), representing the amount of clot strength generated during clot growth; time to maximum rate of lysis (TMRL): defined as the time when maximum amplitude is observed until the time (min) of maximum velocity of clot lysis is observed; maximum rate of lysis (MRL): the greatest velocity of clot lysis (dynes/cm$^2$/sec); CLT: defined as the time (min) from when growth ceases until lysis is complete (amplitude returns to 2 mm).

Figure 3A:
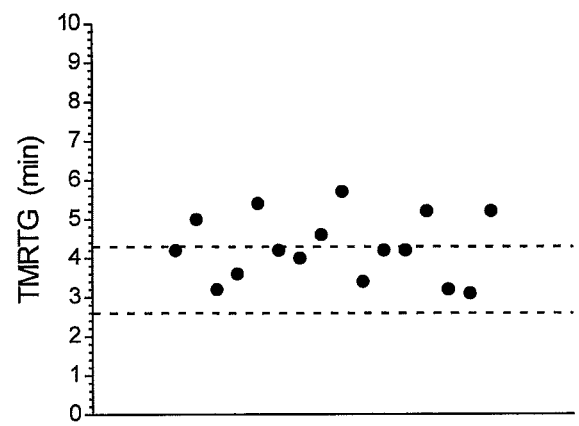
FIGS. 3A-3C are scatter dot graphs showing LVAD patient plasma TMRTG (FIG. 3A), MRTG (FIG. 3B) and TTG data (FIG. 3C). Individual data are represented by each circle. Dashed lines represent the 95% confidence interval values derived from normal individuals as described in the text.
Figure 3B:
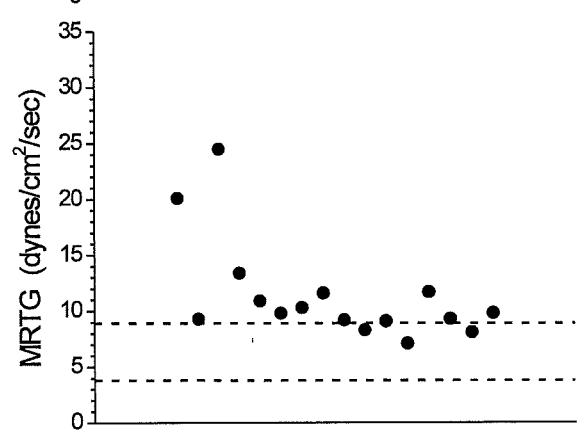
Figure 3C:
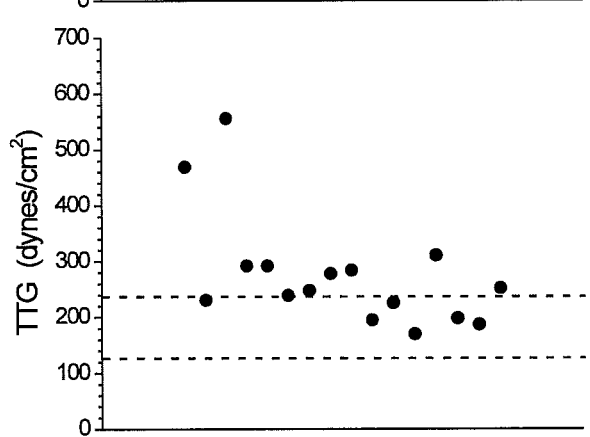
Figure 4A:
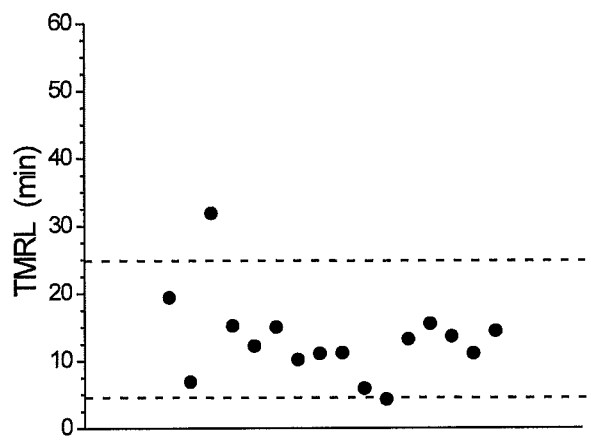
FIGS. 4A-4C are scatter dot graphs showing LVAD patient plasma TMRL (FIG. 4A), MRL (FIG. 4B) and LCT data (FIG. 4C). Individual data are represented by each circle. Dashed lines represent the 95% confidence interval values derived from normal individuals as described in the text.
Figure 4B:
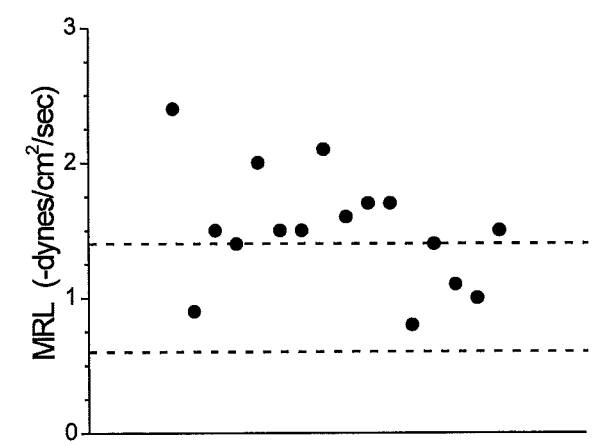
Figure 4C:
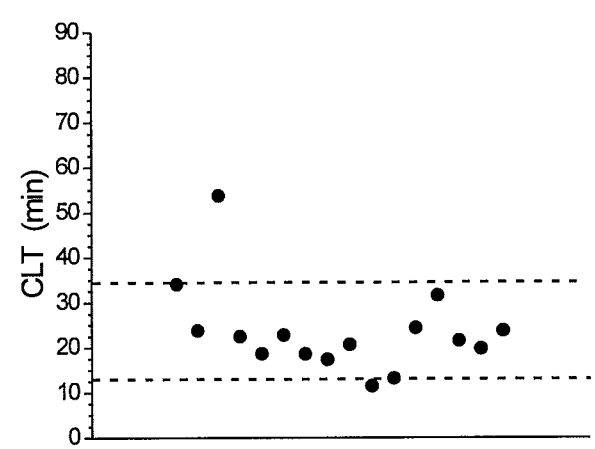

With regard to thrombelastographic data, FIGS. 3A-3C display the coagulation kinetic profile of the LVAD patients. With regard to TMRTG, 37.5% (15.2%-64.6%) of patients had abnormally increased values, indicative of hypocoagulation, likely secondary to warfarin administration. As for MRTG, 81.2% (54.4%-96.0%) of patients had abnormally large values, and in the case of TTG, 62.5% (35.4%-84.8%) had abnormally large values, demonstrating hypercoagulation. FIGS. 4A-4C depict the fibrinolytic kinetic profile of the LVAD patients. With regard to onset of clot lysis, 6.2% (0.2%-32.2%) of patients demonstrated a prolongation of TMRL, which would be consistent with a hypofibrinolytic state. In contrast, 62.5% (35.4%-84.8%) of LVAD patients had an abnormal increase in MRL, indicative of increased vulnerability to lysis. Further, only 6.2% (0.2%-32.2%) of patients had CLT values that were abnormally prolonged or shortened, indicative of hypofibrinolytic and hyperfibrinolytic tendencies in these individuals, respectively. Lastly, 31.2% (11.0%-58.7%) of patients had COHF formation, whereas 75.0% (47.6%-92.7%) had iron-enhanced coagulation.

Coincident comorbid conditions associated with upregulated Hmox activity with coagulation and fibrinolytic data are displayed in Table 8. Three patients had no comorbidities and had neither hypercoagulable nor hypofibrinolytic kinetic profiles, although two of these individuals had either COHF formation or iron-enhanced coagulation. Further, four patients had hypercoagulability with COHF formation and/or iron-enhanced coagulation, but were without any comorbid conditions. In contrast, all nine patients with one or more comorbid states was hypercoagulable, and seven of these patients had concurrent COHF formation and/or iron-enhanced coagulation. Only one patient, with obesity and OSA, had hypofibrinolytic kinetic findings. In sum, the majority of LVAD patients were hypercoagulable, and most of these patients had a comorbid condition with COHF formation and/or iron-enhanced coagulation present.

TABLE 8

Individual patient comorbidity and coagulation characteristics.

| Patient | Obesity | DM | OSA | Hypercoagulable | Hypofibrinolytic | COHF+ | Iron+ | Comorbidity− |
|---|---|---|---|---|---|---|---|---|
| 1 | — | Yes | — | Yes | — | — | Yes | — |
| 2 | — | — | — | Yes | — | — | Yes | Yes |
| 3 | — | — | — | — | — | Yes | — | — |
| 4 | — | Yes | Yes | Yes | — | — | Yes | — |
| 5 | — | Yes | — | Yes | — | — | — | — |
| 6 | — | — | — | Yes | — | — | Yes | Yes |
| 7 | — | — | — | — | — | — | — | — |
| 8 | Yes | — | — | Yes | — | — | Yes | — |
| 9 | Yes | — | — | Yes | — | — | — | — |

TABLE 8-continued

Individual patient comorbidity and coagulation characteristics.

| Patient | Obesity | DM | OSA | Hypercoagulable | Hypofibrinolytic | COHF+ | Iron+ | Comorbidity− |
|---|---|---|---|---|---|---|---|---|
| 10 | — | — | — | Yes | — | — | Yes | Yes |
| 11 | — | — | — | Yes | — | Yes | Yes | Yes |
| 12 | Yes | — | Yes | Yes | Yes | Yes | Yes | — |
| 13 | — | — | — | — | — | — | Yes | — |
| 14 | — | Yes | Yes | Yes | — | — | Yes | — |
| 15 | Yes | — | — | Yes | — | Yes | Yes | — |
| 16 | — | Yes | Yes | Yes | — | Yes | Yes | — |

DM = diabetes mellitus; OSA = obstructive sleep apnea; obesity = BMI >30 kg/m$^2$; Hypercoagulable = MRTG or TTG values greater than the normal 95% CI value; Hypocoagulable = TMRL or CLT value greater than the normal 95% CI value; COHF+ = positive COHF formation; Iron+ = iron-enhanced coagulation present; Comorbidity− = no DM, OSA or obesity present.

Example 4

Role of Iron in Plasmatic Coagulation in Alzheimer's Disease

Methods

Viscoelastic Plasma Coagulation and Fibrinolysis Analyses. All viscoelastic method-based experimentation was completed at the University of Arizona. To establish normal laboratory ranges for the subsequently described assays, human plasma (George King Bio-Medical, Overland Park, Kans., USA) anticoagulated with sodium citrate was obtained, which was composed of plasma from 30 individuals (15 males, 15 females; mean age 30 years, with range of 20 years to 47 years). All subjects were confirmed to be disease-free, nonsmokers, and not pregnant.

With regard to AD patient samples, they were obtained from a commercial vendor (PrecisionMed, Inc., Solana Beach, Calif., USA). This vendor collects various body fluids (e.g., cerebral spinal fluid, blood) from patients being monitored over time that are diagnosed with minimal cognitive impairment (MCI) or Alzheimer's disease. The patient centers involved are located throughout the United States, with ethical oversight provided by the Western Institutional Review Board (Puyallup, Wash., USA). The protocol number for this particular study was #8009. The AD patients had to meet the following criteria for inclusion: mini mental state exam (MMSE) score ≥14 to ≤28; sign an approved written consent; agree to venipuncture; be ≥50 years of age; have a brain magnetic resonance imaging or computed tomographic study excluding other causes of neurological compromise; Hachinski score ≤4; have a diagnosis of dementia or MCI established by clinical exam and documented by MMSE and other neuropsychological exams. For this specific study, AD patients were nonsmokers, have no congenital bleeding abnormality and were anticoagulated. After these inclusion criteria were met, whole blood (5 ml) was obtained from a peripheral vein on one of the patients' arms. The blood sample was anticoagulated with sodium citrate (9 parts blood to 1 part 0.105M sodium citrate), centrifuged at 3000×g for 15 min at room temperature, with plasma removed, aliquoted and placed at −80° C. before transport to the University of Arizona. After all plasma samples were collected, they were sent on dry ice and kept at −80° C. prior to experimentation.

Coagulation Analyses and Carboxyhemefibrinogen (COHF) Assay.

Plasma samples were thawed to 37° C. just prior to analysis. Mixture volume for subsequently described samples was 359.4 µl. Samples were composed of 326 µl of plasma; 10 µl of tissue factor (0.1% final concentration in dH$_2$O; Diagnostica Stago S.A.S., Asnieres sur Seine, France), 3.6 µl of dH$_2$O or CORM-2 (CO releasing molecule-2; tricarbonyldichlororuthenium (II) dimer, 100 µM final; Sigma-Aldrich, Saint Louis, Mo., USA) and 20 µl of 200 mM CaCl$_2$ as previously noted in our COHF assay (Nielsen et al., *Blood Coagul Fibrinolysis* 22:657-661 (2011); Matika et al., *ASAIO J* 60:716-721 (2014); Thompson et al., epub ahead of print (2014)). This amount of CORM-2 increases clot strength in a standardized manner when CO is not present in detectable concentrations (Nielsen et al., *Blood Coagul Fibrinolysis* 22:657-661 (2011); Matika et al., *ASAIO J* 60:716-721 (2014); Thompson et al., epub ahead of print (2014)). Mixtures were pipetted into disposable plastic cups in a computer-controlled thrombelastograph (Model 5000, Haemoscope Corp., Niles, Ill., USA), with CaCl$_2$ added to commence coagulation. Data were collected at 37° C. for 15 min. The elastic modulus-based parameters previously described (Nielsen et al., *Blood Coagul Fibrinolysis* 22:657-661 (2011); Matika et al., *ASAIO J* 60:716-721 (2014); Thompson et al., epub ahead of print (2014)) were determined, as detailed in the description of FIGS. 5A-5C.

Utilizing this technique, hypercoagulability was defined as a total thrombus generation (TTG) value >95% confidence interval value of the normal plasma data set. The presence of COHF was defined as the % increase in TTG via CORM-2 exposure that was less than the average of such measurements in normal plasma samples. For this series the value used to define COHF presence was determined to be an increase in TTG of <89%.

Iron-Enhanced Coagulation Detection Assay. Plasma mixtures were composed of 320 µl of plasma, 20 µl dH$_2$O or deferoxamine (5.6 mM final; Sigma-Aldrich) that were incubated at 37° C. for 15 min in the thrombelastograph cups, before adding 20 µl of 200 mM CaCl$_2$ (Matika et al., *ASAIO J* 60:716-721 (2014); Thompson et al., *J Thromb Thrombolysis* epub ahead of print (2014)). Data were collected until the alpha value of the mixture was obtained, with comparison of the maximum rate of thrombus generation (MRTG) values being the indicator of iron-mediated coagulation enhancement as previously noted (Matika et al., *ASAIO J* 60:716-721 (2014); Thompson et al., *J Thromb Thrombolysis* epub ahead of print (2014)). The nonspecific decrease in MRTG value secondary to deferoxamine addition was determined by the difference in the mean between ten replicates of two conditions (without and with deferoxamine) in pooled normal plasma (George King Bio-Medical) plus two standard deviations of the deferoxamine exposed replicates—this summated to a decrease of 1.2 dynes/cm$^2$/sec. Thus, a decrease in MRTG>1.2 dynes/cm$^2$/sec after deferoxamine exposure would define the presence of iron-mediated coagulation enhancement (upper limit of normal; lower limit of normal <−0.8 dynes/cm$^2$/sec).

Fibrinolytic Kinetic Analyses. Plasma samples were thawed to 37° C. prior to analysis. The final mixture volume was 360 μl. The mixture was composed of 320 μl of plasma; 10 μl of tissue factor (0.1% final concentration in $dH_2O$; Diagnostica Stago S.A.S.), 10 μl of tissue type plasminogen activator (tPA, 580 IU/μg, Genentech, Inc., San Francisco, Calif., USA; 100 IU/ml final), and 20 μl of 200 mM $CaCl_2$ (Matika et al., *ASAIO J* 60:716-721 (2014); Thompson et al., *J Thromb Thrombolysis* epub ahead of print (2014)). Mixtures were placed in a disposable plastic cup in a thrombelastograph (Model 5000, Haemoscope Corp.), with $CaCl_2$ added as the last step. Data were collected until clot lysis time (CLT) at 37° C. was observed. Elastic modulus-based parameters of fibrinolysis were documented as previously noted (Matika et al., *ASAIO J* 60:716-721 (2014); Thompson et al., *J Thromb Thrombolysis* epub ahead of print (2014)), with details outlined in the description of FIGS. 6A-6C.

SEM-Based Analyses. All SEM-based studies were performed at the University of Pretoria. Ethical approval was granted by the Health Sciences Ethical committee of the University of Pretoria and written, informed consent was obtained from family members who act as guardians of the patients. Healthy individuals also filled in consent forms. Blood was obtained from three healthy, female subjects after written, informed consent was obtained. They were neversmokers, 25, 26 and 44 years old. Their plasma ferritin (range 2.6-3.3 g/L), serum ferritin (range 13-28 ng/ml) and iron saturation of ferritin (range 19-33%) were normal. As noted previously, forty ml of whole blood was obtained, anticoagulated (sodium citrate, 9 parts blood to 1 part 0.105M sodium citrate), and platelet rich plasma (PRP) was generated by centrifugation of blood at 1250×g for 2 min (Nielsen et al., *Blood Coagul Fibrinolysis* 25:695-702 (2014); Nielsen et al., *Blood Coagul Fibrinolysis* 25:845-50 (2014)).

Using a methodology previously noted to create extensive fibrin fiber networks, PRP smears with different compound exposures were made on glass cover slips and incubated at 37° C. for 8 minutes. A 10 mM CORM-2 stock solution was prepared by mixing 1 mg CORM-2 and 195 ul 100% DMSO, from here on referred to as stock A. Stock A was used to prepare a 1 mM CORM-2 solution by adding 100 ul of stock A to 900 ul of phosphate buffered solution (PBS), form hereon referred to as stock B. Stock B was used in the following in the ratios shown in Table 9 and incubated with PRP for 5 minutes. PRP smears after exposure to different compounds (see Table 9) were made on glass coverslips.

TABLE 9

Preparation methods for extensive fibrin fiber networks of healthy plasma with added $FeCl_3$ and CORM-2.

1. Preparation of and reaction mixture of control plasma; 10 ul PRP + 5 ul thrombin (10 U/ml human thrombin in $ddH_2O$) mixed and incubated for 3 minutes.
2. Preparation of and reaction mixture of iron exposed plasma; 10 ul PRP + 5 ul FeCl3 (1 mM), mixed; addition of 5 ul of thrombin, mixed and incubated 3 min.
3. Preparation of CORM-2 with PRP and reaction mixture of CORM-2 exposed plasma; 10 ul of stock B CORM-2 + 990 ul PRP; then 20 ul of PRP exposes to CORM-2 + 10 ul thrombin, mixed and incubated for 3 minutes.

The cover slips were placed in 0.075 M PBS on a shaker and washed for 20 minutes. The samples were then fixated for 30 minutes followed by three washing steps in 0.075 M PBS for three minutes to remove any residual fixative. The smears were then post-fixated for 15 minutes with 1% osmium tetroxide ($OsO_4$), followed by a washing process, for three minutes in 0.075M PBS. The samples were finally dehydrated serially in 30%, 50%, 70%, 90% and then three times in 100% ethanol followed by drying using hexamethyldisilazane; mounting and coating with carbon. Once the samples had been coated they were analyzed with a scanning electron microscope (Zeiss ULTRA plus FEG SEM, Carl Zeiss Microscopy GmbH, Jena, Germany).

Blood was obtained from AD patients (n=12) that were diagnosed by qualified medical practitioners. All AD individuals were diagnosed using the MMSE. The AD patients were divided into 2 groups (normal and high serum ferritin concentrations, high ferritin being defined as a level of >120 ng/ml for females and >250 ng/ml for males). The AD patients did not have any chronic medical conditions, were nonsmokers, and the age of these patients was 78±12 (mean±SD) years. Fibrin fiber networks were generated as per the same methods described for healthy individuals, but without addition of iron or CORM-2.

After visualization of the fibrin networks with SEM, micrographs were obtained at 40,000 times machine magnification. A representative micrograph of each sample was selected, and subsequently a 10×5 grid was superimposed onto the picture. One fiber was randomly selected out of every block of the grid, ensuring that fiber measurements were not duplicated, and that fibers were systematically assessed to prevent observer bias (Pretorius *Ultrastruct Pathol* 35(4):150-154 (2001); Pretorius et al., *Blood Coagul Fibrinolysis* 22(8):696-700 (2011)). Fibrin fiber thickness was measured with ImageJ (ImageJ is a public domain, Java-based image processing program developed at the National Institutes of Health: http://rsbweb.nih.gov/ij/). From each sample, 50 fibers were measured.

Statistical Analyses and Graphics. Data are presented as mean±SD, individual parameter values, % incidence with 95% confidence intervals (CI), or simply 95% CI. Coagulation and fibrinolysis parameters of AD patient samples were compared with 95% confidence intervals generated from normal plasma. A statistical program was used for student's t-test analyses of differences in fibrin polymer fiber widths (SigmaStat 3.1, Systat Software, Inc., San Jose, Calif., USA). Graphics depicting viscoelastic data were generated with a commercially available program (OrigenPro 7.5, OrigenLab Corporation, Northampton, Mass., USA; CorelDRAW12, Corel Corporation, Mountain View, Calif., USA).

Results

Viscoelastic Analyses. Eleven AD patients (7 male), aged 73±10 years, with MMSE values of 20±3 and body mass index (BMI) values of 24±3 $kg/m^2$ were recruited. In regard to comorbidities, no patient had diabetes mellitus, one had a history of migraine, one had a history of myocardial infarction, four had hypertension, and one had a history of asthma. Ten patients were originally requested for the study, but an additional patient had blood collected, so the vendor was kind enough to donate the plasma and clinical information of this patient for the study.

As for normal plasma values, the 95% confidence interval values for coagulation and fibrinolytic parameters are depicted in Table 10. For an AD patient to be considered hyper/hypocoagulable or hyper/hypofibrinolytic, the kinetic parameter value of interest had to be outside the normal 95% CI values. The criteria for COHF formation and iron enhancement of coagulation were presented in the materials and methods section previously.

TABLE 10

Normal 95% CI values for coagulation and fibrinolytic kinetic parameters.

| Parameter | Values |
|---|---|
| TMRTG (min) | 2.6-4.3 |
| MRTG (dynes/cm$^2$/sec) | 3.8-8.9 |
| TTG (dynes/cm$^2$) | 127-237 |
| TMRL (min) | 3.6-24.9 |
| MRL (dynes/cm$^2$/sec) | 0.6-1.4 |
| CLT (min) | 13.0-34.5 |

Time to maximum rate of thrombus generation (TMRTG): this is the time interval (min) observed prior to maximum speed of clot growth; Maximum rate of thrombus generation (MRTG): this is the maximum velocity of clot growth observed (dynes/cm2/sec); Total thrombus generation (TTG): this is the total area under the velocity curve during clot growth (dynes/cm2), representing the amount of clot strength generated during clot growth; time to maximum rate of lysis (TMRL): defined as the time when maximum amplitude is observed until the time (min) of maximum velocity of clot lysis is observed; maximum rate of lysis (MRL): the greatest velocity of clot lysis (dynes/cm2/sec); CLT: defined as the time (min) from when growth ceases until lysis is complete (amplitude returns to 2 mm).

Figures 5A, 5B, 5C:
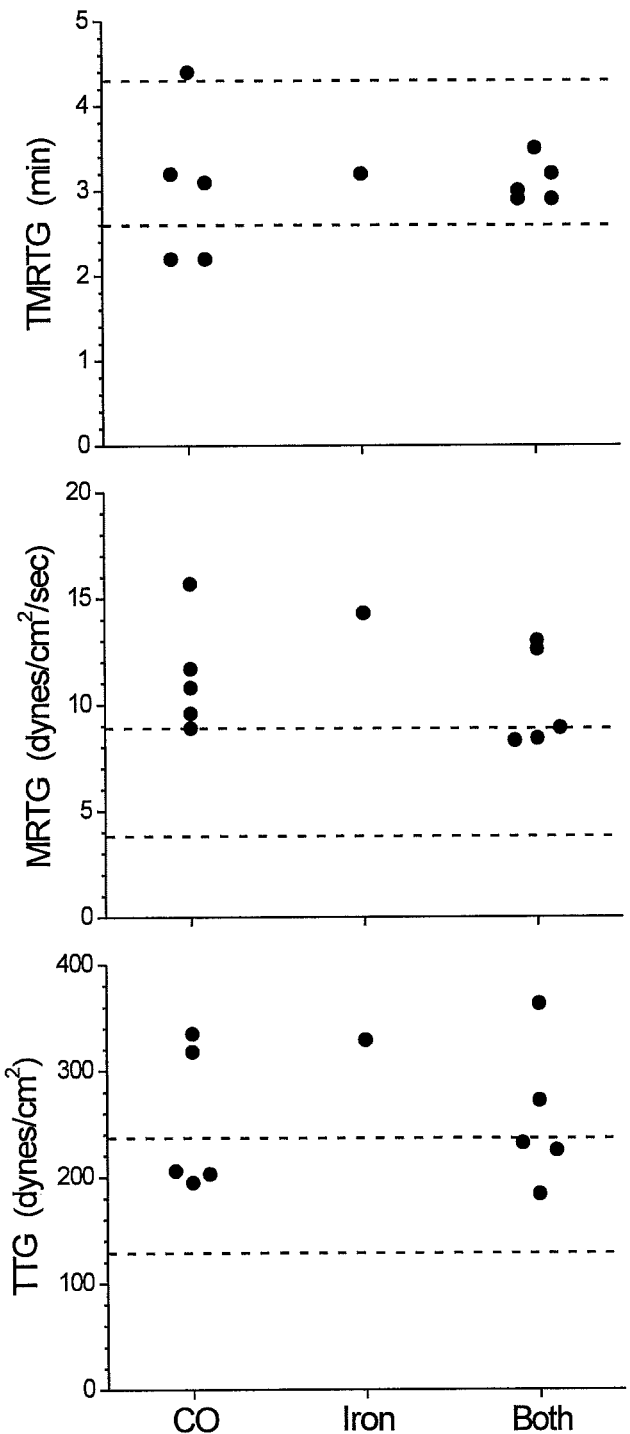
FIGS. 5A-5C are scatter dot graphs showing the effect of Alzheimer's disease on TMRTG (FIG. 5A), MRTG (FIG. 5B) and TTG (FIG. 5C) stratified by modulation of coagulation by CO, iron, or both. Time to maximum rate of thrombus generation (TMRTG): this is the time interval (min) observed prior to maximum speed of clot growth; maximum rate of thrombus generation (MRTG): this is the maximum velocity of clot growth observed (dynes/cm$^2$/sec); and total thrombus generation (TTG, dynes/cm$^2$), the final viscoelastic resistance observed after clot formation. Individual data are represented by each circle. Dashed lines represent the 95% confidence interval values for coagulation derived from normal individuals as described in the text. All patients had modification of coagulation by CO, iron, or both; the primary kinetic abnormalities present were large rates of clot formation and greater than normal clot strength.

FIGS. 5A-5C display the coagulation profiles of the AD patients stratified by COHF formation (CO enhancement of coagulation), enhancement of coagulation by iron, or enhancement of coagulation by both CO and iron. Of interest, there was no patient without modulation of coagulation by either CO or iron. With regard to CO, ten of eleven patients had COHF formation, whereas seven patients had iron-enhanced coagulation kinetics. With regard to TMRTG, one patient had a hypocoagulable TMRTG value, two patients had hypercoagulable TMRTG values, with the remainder within the normal range. As for MRTG, seven patients had hypercoagulable values, two patients had values exactly at the 95% CI value of normal, with the balance within normal range. In the case of TTG, five patients had abnormally strong thrombi, with the balance being within the normal range.

Figures 6A, 6B, 6C:
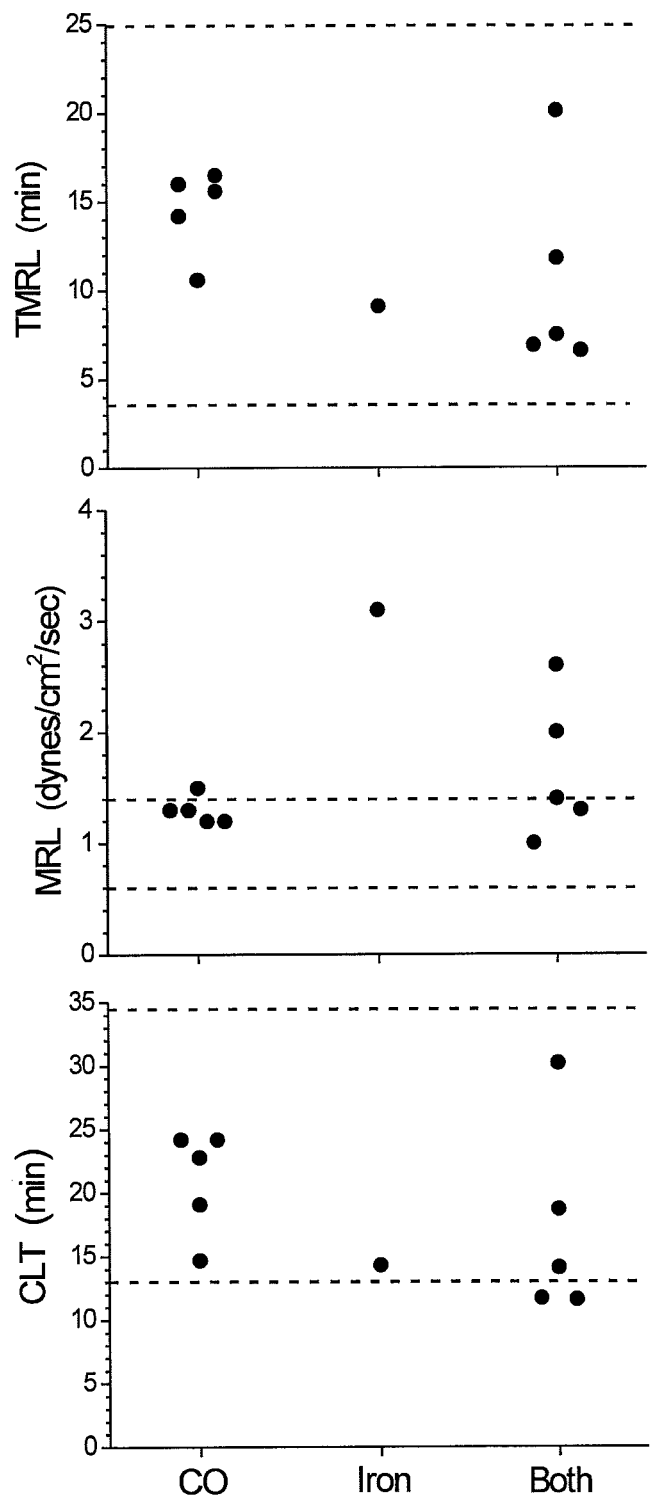
FIGS. 6A-6C are scatter dot graphs showing the effect of Alzheimer's disease on TMRL (FIG. 6A), MRL (FIG. 6B) and CLT (FIG. 6C) stratified by modulation of fibrinolysis by CO, iron, or both. Time to maximum rate of lysis (TMRL, min), maximum rate of lysis (MRL, dynes/cm$^2$/sec) and clot lysis time (CLT, the time to reach 2 mm amplitude after maximum amplitude is achieved). Individual data are represented by each circle. Dashed lines represent the 95% confidence interval values for fibrinolysis derived from normal individuals as described in the text. While most patients had a normal fibrinolytic kinetic profile, a few demonstrated enhanced vulnerability to clot lysis demonstrated by an abnormally increased rate of clot lysis and decreased clot lysis time.

FIGS. 6A-6C display the fibrinolysis profile data of AD patients stratified as seen in FIGS. 5A-5C. With regard to onset of clot lysis, all AD patients had normal TMRL values. However, four AD patients had an above normal increase in MRL values, indicating an increased vulnerability to lysis, while the remainder of the group had values in the normal range. Lastly, only two of the eleven AD patients had CLT values that were below normal values, indicative of a hyperfibrinolytic tendency in these individuals.

SEM-Based Analyses. The AD cohort from the University of Pretoria was composed of ten women and two men; the normal ferritin group had a serum ferritin concentration of 66±33 ng/ml whereas the high ferritin group had a significantly higher (P=0.0003) ferritin concentration of 253±88 ng/ml.

Figure 7:
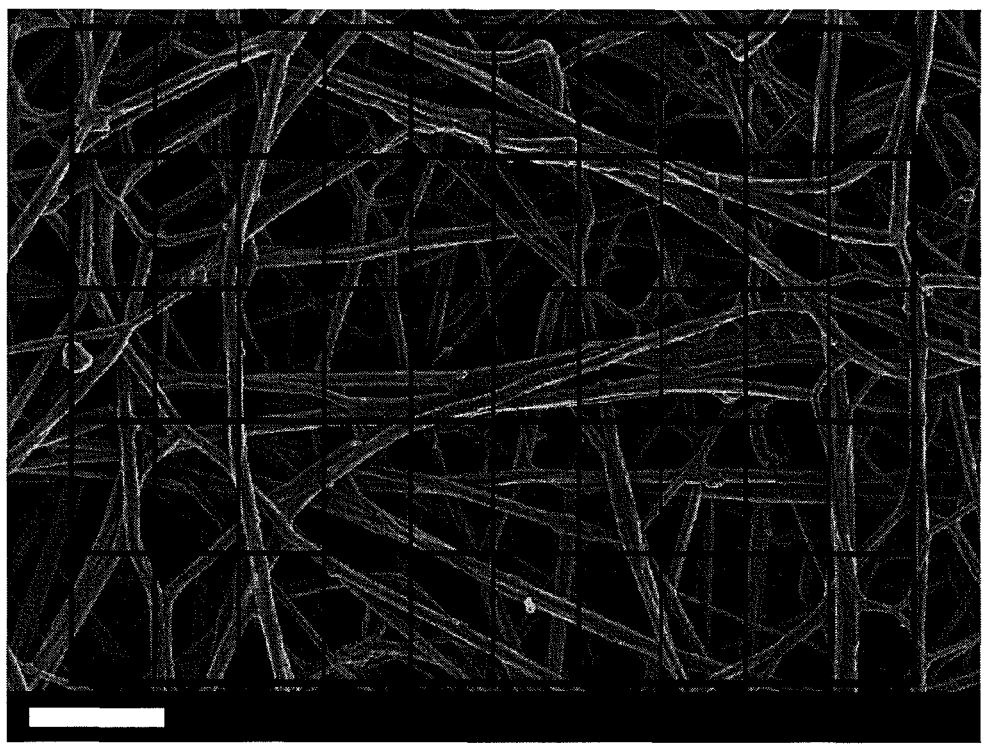
FIG. 7 shows a healthy fibrin fiber network. Plasma with thrombin added to create an extensive fibrin network is depicted. Ten μl of plasma was added to 5 μl thrombin (10 U/ml human thrombin in ddH$_2$O), mixed and incubated for 3 minutes to create an extensive fibrin network. Individual fibrin fibers are visible. A typical 5 by 10 grid is superimposed, which was used to assess fibrin fiber diameter as discussed in the text. Scale bar=1 μm.

With regard to SEM data, FIG. 7 shows a typical, normal subject fibrin network with mostly major, thick fibrin fibers. In healthy individuals, individual fibrin fibers are visible, appearing like a net, with no fused fibers and no fine, lattice-like appearance. When FeCl$_3$ is added to PRP followed by exposure to thrombin, (FIG. 8A) a finer fiber lattice net is observed (see thick white arrow), as well as areas forming a denser mesh (see *), where the lattice net fuses to form a matted deposit. Close examination revealed areas of denser fibrin deposits (*), consisting of fine fibers (see thin white arrow) that were packed closely to each other.

Figures 8A, 8B:
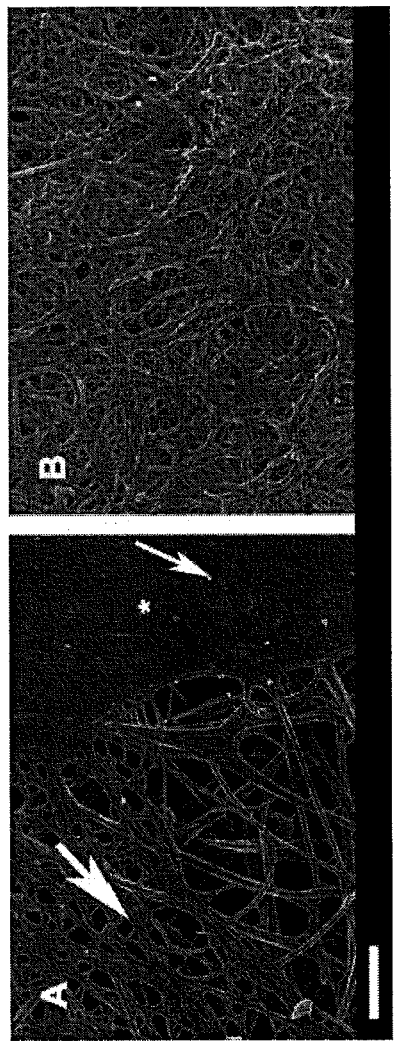
FIGS. 8A and 8B show a healthy fibrin network with added FeCl$_3$ (FIG. 8A) and CORM-2 (FIG. 8B) and thrombin to create an extensive fibrin network.
Figure 9A:
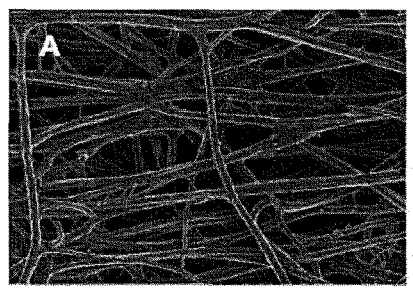
FIGS. 9A-9F show fibrin fiber networks of six AD patients with normal serum ferritin levels. Ten μl of AD plasma was added to 5 μl thrombin (10 U/ml human thrombin in ddH$_2$O), mixed and incubated for 3 minutes to create an extensive fibrin network. Healthy values for ferritin are 20 to 250 ng/ml for males and 10 to 120 ng/mL for females. Globular areas, similar to that observed with CORM-2 exposure are indicated with arrows. Thus, more of a CO effect on fibrin polymer formation is likely. Scale bar=1 μm.
Figure 9B:
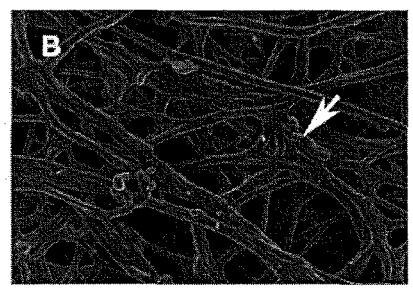
Figure 9C:
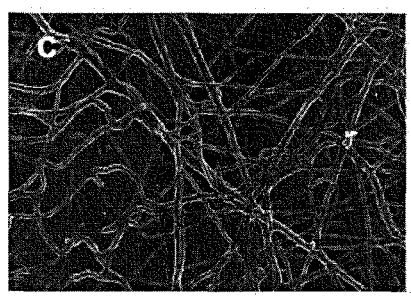
Figure 9D:
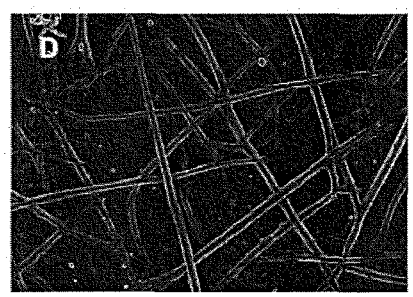
Figure 9E:
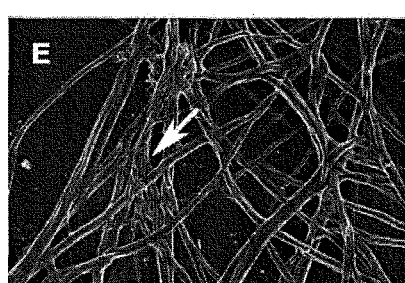
Figure 9F:
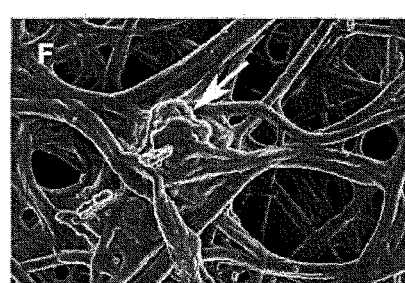
Figure 10A:
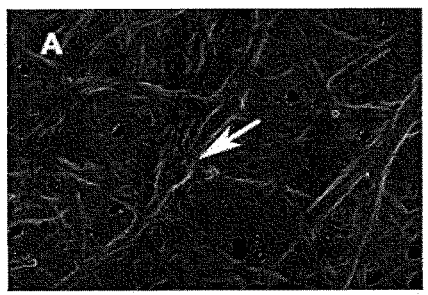
FIGS. 10A-10F show fibrin fiber networks of six AD patients with high serum ferritin levels. Ten μl of AD plasma was added to 5 μl thrombin (10 U/ml human thrombin in ddH$_2$O), mixed and incubated for 3 minutes to create an extensive fibrin network. Globular areas, similar to that observed with CORM-2 exposure are indicated with arrows. Unlike patients' clots in FIGS. 9A-9F, both fine fiber lattice and globular areas are present, consistent with a combination of iron and CO-mediated changes in fibrin polymer formation. Scale bar=1 μm.
Figure 10B:
Figure 10C:
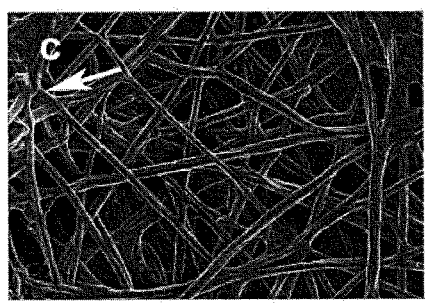
Figure 10D:
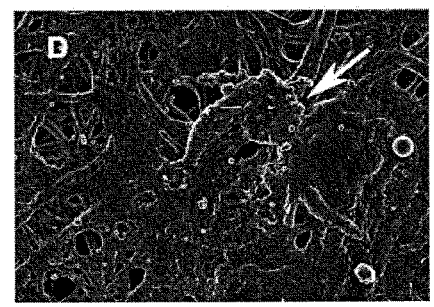
Figure 10E:
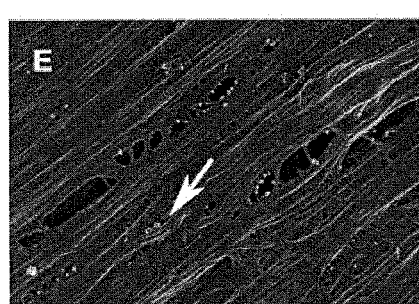
Figure 10F:

Addition of CORM-2 to PRP, followed by exposure to thrombin, resulted in fibrin fiber diameters that were also decreased compared to the healthy fibers but were more densely packed, with a more globular structure compared to the rather straight individual fibers seen in the healthy fibrin structure (FIG. 8B). This ultrastructure was suggestive of CORM-2 modifying the fibrin packaging.

FIGS. 9A-9F show fibrin networks from the individual AD patients with normal serum ferritin levels. Here the fiber diameter increases. FIGS. 10A-10F show fibrin networks of Alzheimer's patients with high serum ferritin levels. The fibrin fiber nets resemble those seen in FIG. 8A (FeCl$_3$ is added to PRP followed by thrombin exposure), where the net resembles a fine lattice. The individual fibrin fibers of both the normal and high serum ferritin AD individuals showed a more globular morphology, as seen with CORM-2, instead of the rather straight and smooth individual fibers seen in the healthy subject fibrin fibers. See arrows indicating globular structure in FIGS. 9A-9F and 10A-10F.

Figure 11:
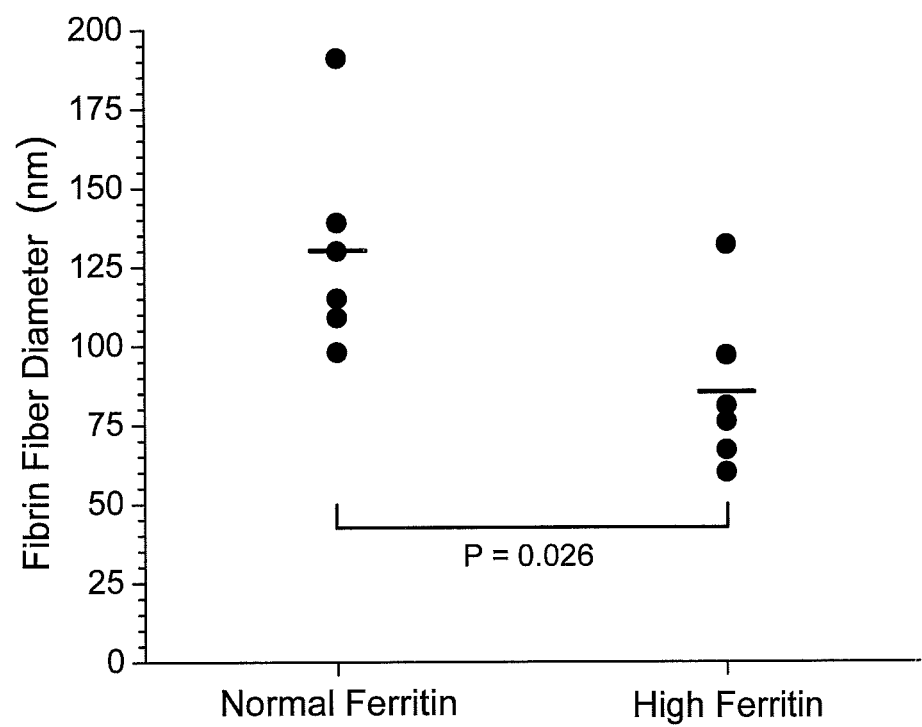
FIG. 11 shows a comparison of fibrin fiber diameter in AD patients with normal or high serum ferritin concentrations. Individual patient data are depicted as black dots; the small horizontal bars are the group mean values. AD patients with high serum ferritin concentrations had significantly smaller diameter fibrin strands compared to those with normal ferritin concentrations as indicated by the large horizontal bar. This difference is consistent with iron modification of fibrin polymer formation.
Figure 12:
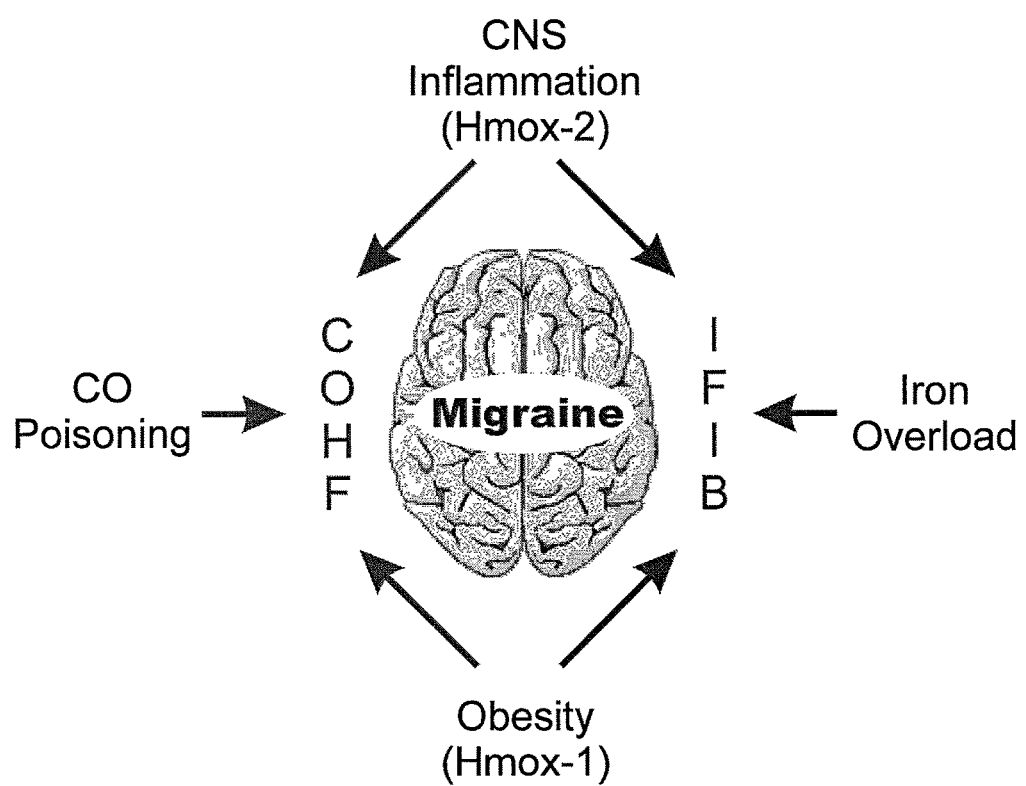
FIG. 12 shows the paradigm of the relationship of carbon monoxide (CO) and iron to migraine headache. CO and iron derived from environmental or endogenous sources combine with fibrinogen to form carboxyhemefibrinogen (COHF) or iron-bound fibrinogen (IFIB), which enhances plasmatic coagulation. Hmox=heme oxygenase; Hmox-1 is the inducible isoform, and Hmox-2 is the constitutive isoform.

With regard to average fibrin fiber width, the value for the normal subjects was 105±3 nm. Exposure to FeCl$_3$ decreased fiber width by 58% and exposure to CORM-2 decreased width by 43%. The average width values for the AD patients, stratified by serum ferritin concentration, is depicted in FIG. 11. The high ferritin AD group had a fiber width that was significantly less than the normal ferritin AD group, with an average value 34% less than the high ferritin group.

Example 5

Role of Iron-induced Plasmatic Coagulation in Patients with Chronic Migraine (CM)

Methods

CM Patient Plasma. Written, informed consent was obtained from all subjects prior to experimentation. Patients undergoing periodic evaluation and treatment at one of our outpatient clinics for CM, aged 18 or more years of age, and not being administered anticoagulants chronically, were recruited for this investigation. Patients could not be recruited if they were being administered valproic acid for their headache, as it is a Hmox inhibitor (Kwon et al., *Neurochem Int* 62:240-250 (2013)). Given recent experiences with investigating upregulation of Hmox with iron-enhanced coagulation, 20 to 30 patients were sought to detect such changes in the setting of CM (Nielsen et al., *Blood Coagul Fibrinolysis* 26(2):200-204 (2015); Matika et al., *ASAIO J* 60:716-721 (2014); Nielsen et al., *Curr Neurovasc Res* epub ahead of print (2015)). The patients had no history of inherited bleeding disorder, and they could not be current tobacco smokers. After written consent was obtained, the concentration of COHb present was recorded via noninvasive pulse oximetry (Model Rad57, Masimo Corporation, Irvine, Calif., USA; accuracy ±1% as per manufacturer specifications). A COHb reading was obtained from two fingers of each hand, with an average of the four readings used as the final value. A sample of whole blood (5 ml) was obtained from the patients via peripheral venipuncture in either upper limb This blood sample was anticoagulated with sodium citrate (9 parts blood to 1 part 0.105M sodium citrate) and subsequently centrifuged at 3000×g for 15 min at room temperature, with plasma decanted, aliquoted and immediately frozen on dry ice at the outpatient facility. The samples were subsequently transported back to the University of Arizona Department of Anesthesiology laboratories and stored at −80° C. prior to experimentation.

Normal Individual Reference Plasma. Individual plasma samples obtained (George King Bio-Medical, Overland Park, Kans., USA) anticoagulated with sodium citrate (9 parts blood to 1 part 0.105M sodium citrate during processing) were utilized for experimentation. A standard lot of 30 individuals (15 males, 15 females; mean age 30 years, with range of 20 years to 47 years) were utilized. All normal subjects were verified to be without blood borne disease (e.g., hepatitis), not pregnant, and nonsmokers as per the vendor's specifications. The rationale for using plasma of this nature is that standard, plasma-based tests of coagulation (e.g., prothrombin time, activated prothrombin time, fibrinogen concentration, and coagulation factor activities) commonly have 95% confidence interval values in clinical pathology laboratories within hospitals/ambulatory clinics established with such material.

Coagulation Kinetic Analyses and COHF Assay. Plasma was rapidly thawed at 37° C. on the day of experimentation. The final volume for all subsequently described plasma sample mixtures was 359.4 µl. Sample composition consisted of 326 µl of plasma; 10 µl of tissue factor reagent (0.1% final concentration in distilled water; Diagnostica Stago S.A.S., Asnieres sur Seine, France), 3.6 µl of distilled water or CORM-2 (carbon monoxide releasing molecule-2; tricarbonyldichlororuthenium (II) dimer, 100 µM final concentration; Sigma-Aldrich, Saint Louis, Mo., USA) and 20 µl of 200 mM $CaCl_2$ as per our previously described COHF assay (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)). Plasma sample mixtures were placed in a disposable cup in a computer-controlled thrombelastograph® hemostasis system (Model 5000, Haemoscope Corp., Niles, Ill., USA), with addition of $CaCl_2$ as the last step to initiate clotting. Data were collected at 37° C. for 15 min. The following elastic modulus-based parameters previously described were determined: time to maximum rate of thrombus generation (TMRTG): this is the time interval (min) observed prior to maximum speed of clot growth; maximum rate of thrombus generation (MRTG): this is the maximum velocity of clot growth observed (dynes/cm$^2$/sec); and total thrombus generation (TTG, dynes/cm$^2$), the final viscoelastic resistance observed after clot formation (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)).

Using this method, hypercoagulability was subsequently described as a TTG value >95% confidence interval value of the normal subjects data set. The presence of COHF was defined as the % increase in TTG secondary to CORM-2 exposure that was less than the average value of similar measurements in normal subject samples. For this series the value used to define COHF presence was determined to be an increase in TTG of <89%.

IFIB Detection Assay. Plasma samples consisted of 320 µl of plasma, 20 µl $dH_2O$ or deferoxamine (5.6 mM final concentration; Sigma-Aldrich, Saint Louis, Mo., USA) that were incubated for 15 min at 37° C. in the thrombelastograph cups, prior to addition of 20 µl of 200 mM $CaCl_2$ (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)). Data were collected until the angle of the sample was determined, with comparison of the MRTG the primary determinant of iron-mediated enhancement of coagulation via IFIB formation as previously described (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)). The normal, nonspecific amount of decrease in MRTG secondary to deferoxamine exposure was defined by the differences in the means between ten replicates of the two conditions (without and with deferoxamine) in pooled normal plasma (George King Bio-Medical, Overland Park, Kans., USA) plus two standard deviations of the deferoxamine exposed replicates—this amounted to a decrease of 1.2 dynes/cm$^2$/sec. Thus, a decrease in MRTG>1.2 dynes/cm2/sec after deferoxamine exposure would define the presence of iron-mediated enhancement of coagulation (upper limit of normal; lower limit of normal was <−0.8 dynes/cm2/sec).

Fibrinolytic Kinetic Analyses. Plasma was rapidly thawed at 37° C. on the day of experimentation. The final volume for all subsequently described plasma sample mixtures was 360 µl. Sample composition consisted of 320 µl of plasma; 10 µl of tissue factor reagent (0.1% final concentration in $dH_2O$; Diagnostica Stago), 10 µl of tissue type plasminogen activator (tPA, 580 IU/µg, Genentech, Inc., San Francisco, Calif., USA; 100 IU/ml final concentration), and 20 µl of 200 mM $CaCl_2$ as described previously (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)). Plasma sample mixtures were placed in a disposable cup in a computer-controlled thrombelastograph® hemostasis system (Model 5000, Haemoscope Corp., Niles, Ill., USA), with addition of $CaCl_2$ as the last step to initiate clotting. Data were collected at 37° C. until clot lysis time (CLT) was observed. Elastic modulus-based parameters of fibrinolysis recorded included time to maximum rate of lysis (TMRL, min), maximum rate of lysis (MRL, dynes/cm$^2$/sec) and CLT as previously described (Thompson et al., *J Thromb Thrombolysis* epub ahead of print (2015); Matika et al., *ASAIO J* 60:716-721 (2014); Nielsen et al., *Curr Neurovasc Res* epub ahead of print (2015)).

Statistical Analyses and Graphics. Data are presented as mean±SD, as individual parameter values, as % incidence with 95% confidence intervals (CI), or as the coefficient of determination ($R^2$) with corresponding P value. Coagulation and fibrinolysis parameters of CM patient samples were compared with 95% confidence intervals generated from normal plasma. Linear regression comparing COHb, % increase in TTG in response to addition of CORM-2, and decrease in MRTG after chelation individually to BMI values was performed to assess interaction of obesity with these variables. Linear regressions, corresponding $R^2$ values, and graphics depicting viscoelastic data were generated with commercially available programs (OrigenPro 7.5, OrigenLab Corporation, Northampton, Mass., USA; CorelDRAW12, Corel Corporation, Mountain View, Calif., USA).

Results

After 3 separate clinic sessions, 27 CM patients (25 female) were recruited, but blood samples could only be obtained from 26 patients. Only 3 patients had an aura that preceded the headache, and all of them were female. The patient that could not have a blood sample collected secondary to difficulty with venipuncture was 37 years old, had a COHb concentration of 2.5% and a BMI value of 37 kg/m$^2$. Her data were used for correlation of COHb with BMI as subsequently presented. The remaining cohort of 26 patients were 46±12 years old, had a COHb concentration of 2.2±1.4% (range 0.0%-5.3%), and BMI of 29±6 kg/m$^2$ (9 patients with BMI>30 kg/m$^2$). Lastly, 74.1% (53.7%-88.9%) (incidence (95% CI)) of CM patients had COHb>1%.

COHF and IFIB Formation. Three of the 26 patients (11.5% (2.4%-30.2%)) had neither detectable COHF nor IFIB formation. Of the remaining 88.5% (69.8%-97.6%) of CM patients, 11.5% (2.4%-30.2%) had COHF formation only, 19.2% (6.6%-39.4%) had IFIB formation only, and 57.7% (36.9%-76.6%) had both COHF and IFIB formation.

Subsequently presented coagulation and fibrinolytic kinetic data were stratified by involvement of CO, iron, both, or neither.

Figure 13A:
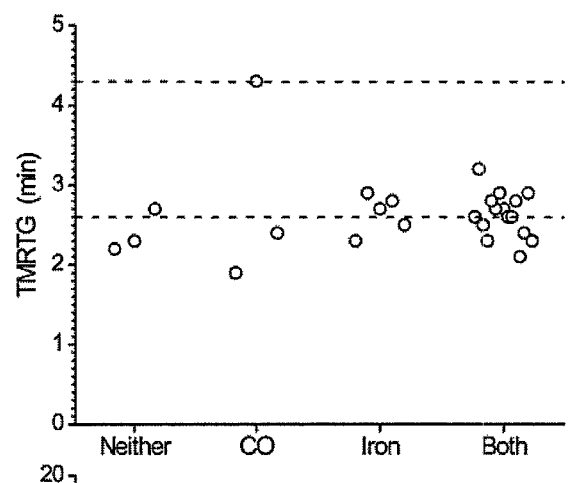
FIGS. 13A-13C show the effect of chronic migraine on TMRTG (FIG. 13A), MRTG (FIG. 13B) and TTG (FIG. 13C) stratified by modulation of coagulation by CO, iron, or both. Time to maximum rate of thrombus generation (TMRTG, min); maximum rate of thrombus generation (MRTG, dynes/cm$^2$/sec); and total thrombus generation (TTG, dynes/cm$^2$). Individual data are represented by each circle. Dashed lines represent the 95% confidence interval values for coagulation derived from normal individuals as described in the text.
Figure 13B:
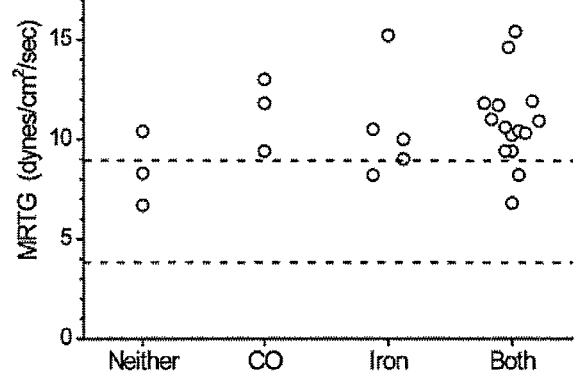
Figure 13C:
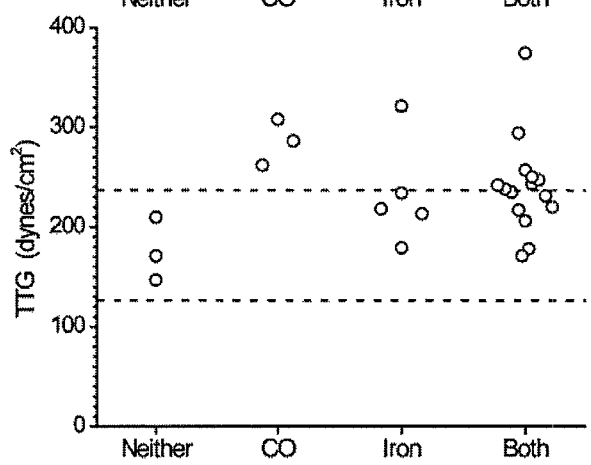

Coagulation Kinetics. Coagulation data are depicted in FIGS. 13A-13C. With regard to TMRTG, 42.3% (23.4%-63.1%) of patients were hypercoagulable, with values below the 95% CI depicted as dashed lines. As for velocity of clot formation, 80.8% (60.6%-93.4%) of CM patients were hypercoagulable. Lastly, 46.2% (26.6%-66.6%) of CM patient plasma samples had abnormally strong clot strength as determined by TTG. Taken as a whole, the majority of CM patients tended to be hypercoagulable as assessed by one or more variable.

Figure 14A:
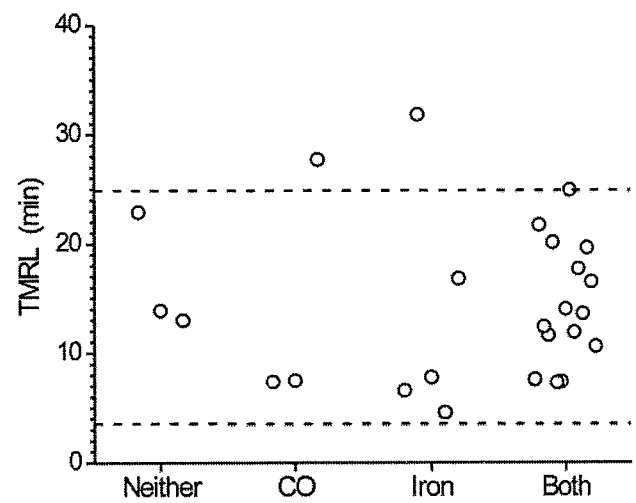
FIGS. 14A-14C show the effect of chronic migraine on TMRL (FIG. 14A), MRL (FIG. 14B) and CLT (FIG. 14C) on fibrinolysis stratified by modulation of coagulation by CO, iron, or both. Time to maximum rate of lysis (TMRL, min), maximum rate of lysis (MRL, -dynes/cm$^2$/sec) and clot lysis time (CLT, the time to reach 2 mm amplitude after maximum amplitude is achieved). Individual data are represented by each circle. Dashed lines represent the 95% confidence interval values for fibrinolytic parameters derived from normal individuals as described in the text.
Figure 14B:
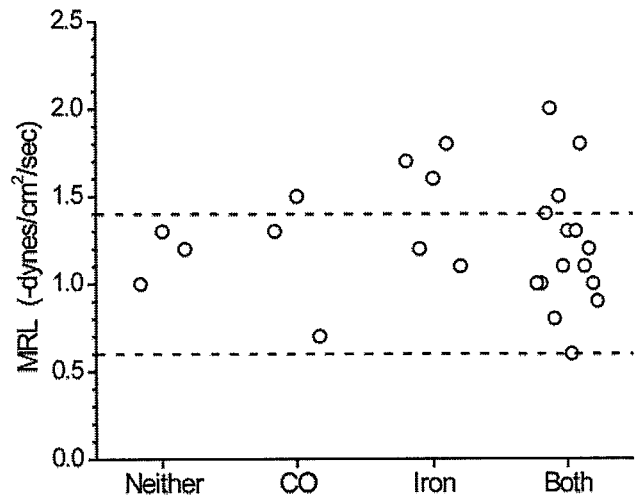
Figure 14C:
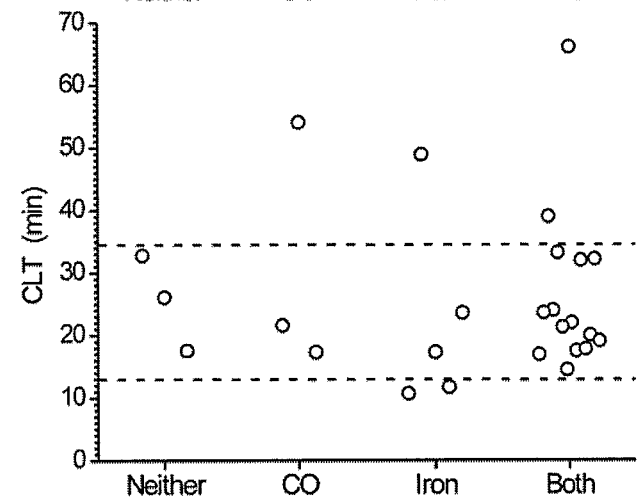

Fibrinolytic Kinetics. Fibrinolytic data are displayed in FIGS. 14A-14C. The time to maximum rate of clot lysis was abnormally prolonged in 7.7% (0.9%-25.1%) of CM patients, a sign of hypofibrinolytic tendencies. Similarly, 15.4% (4.4%-34.9%) of these patients had a prolonged CLT value, indicative of hypofibrinolysis. In contrast, 26.9% (11.6%-47.8%) of chronic migraineurs had abnormally increased MRL values, indicating enhanced fibrinolytic vulnerability. In sum, these patients had a mixed picture of normal, hypofibrinolytic and profibrinolytic tendencies.

Figure 15A:
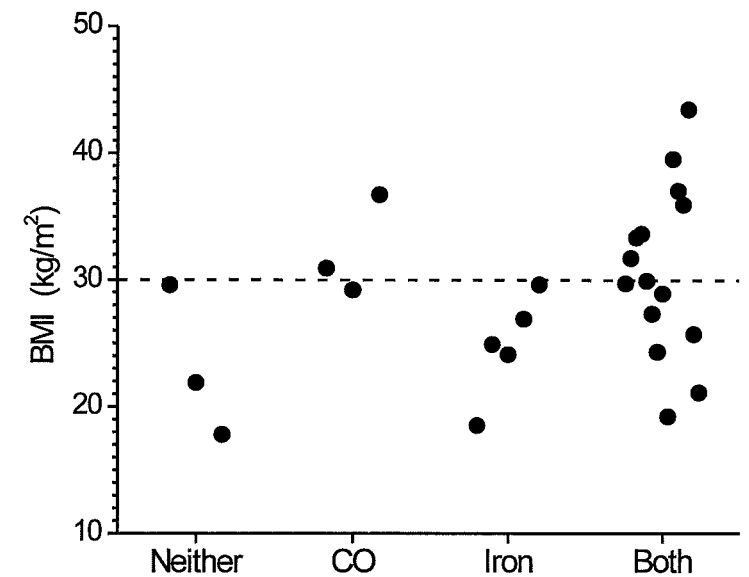
FIGS. 15A and 15B show correlations of BMI with CO and iron modified coagulation. When BMI values are stratified by fibrinogen modification by CO and/or iron, 7 of 9 individuals with BMI values greater than 30 kg/m$^2$ have coagulation modified by CO alone or CO and iron together (FIG. 15A). As BMI value increases, so does resistance to increase clot strength in response to exogenous CO, diagnostic for increased carboxyhemefibrinogen formation potentially released from inflammatory adipose tissue (FIG. 15B).
Figure 15B:
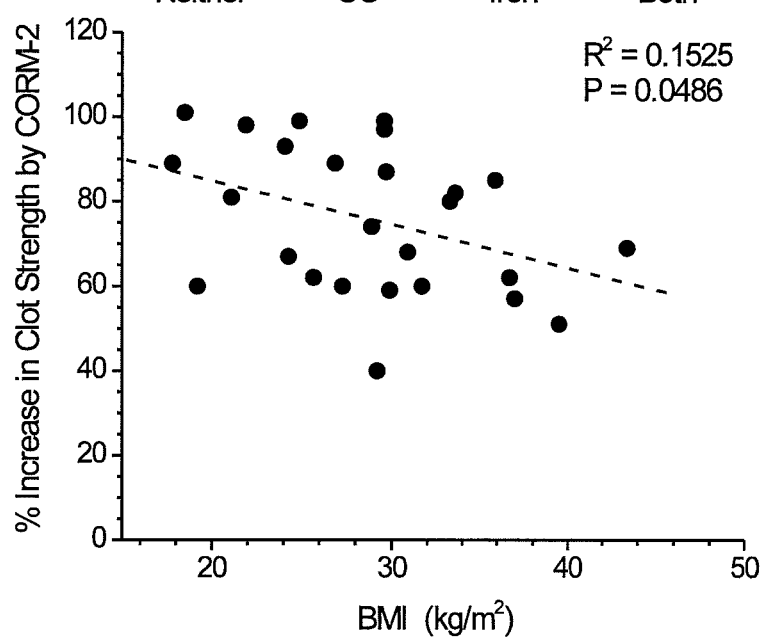

Correlation of BMI to Products of Hmox Activity. Given that several of our patients had BMI values above the threshold known to upregulate Hmox activity (30 kg/m$^2$), the associations of BMI on COHb, COHF formation and IFIB formation were assessed. First, as seen in FIG. 15A, the three patients that had neither CO nor iron effects on their coagulation had BMI values below 30 kg/m$^2$. In contrast, 7 of the 9 patients with BMI values above 30 kg/m$^2$ had both CO and iron-mediated enhancement of coagulation, with the remaining 2 patients with CO-mediated enhancement. With regard to COHb formation, $R^2$=0.1437 (P=0.0511), just missing statistical significance. When iron enhancement of coagulation assessed by changes in MRTG were correlated with BMI values, $R^2$=0.0009 (P=0.8795) was observed, indicating no significant association. Lastly, as depicted in FIG. 15B, BMI did significantly correlate with resistance to change in clot strength in response to CO addition by CORM-2, indicative of an increased endogenous CO concentration with increasing BMI values.

I claim:

1. A method for diagnosing or assisting in diagnosing a subject having or suspected of having an iron-related pathology comprising:
analyzing a plasma sample obtained from an anticoagulated blood sample from the subject to obtain viscoelastic parameters selected from the group consisting of the time to maximum rate of thrombus generation (TMRTG) and maximum rate of thrombus generation (MRTG) of the plasma sample as the sample coagulates in the absence and in the presence of an iron-specific chelator incubated with the sample, wherein incubation of the sample with the iron chelator is effective to chelate iron in the sample before analysis of the sample;
wherein a variation in the viscoelastic parameters of the plasma sample relative to plasma samples from healthy subjects indicates the subject has an iron-related pathology.

2. The method of claim 1, wherein the viscoelastic parameters of the plasma sample from the subject having or suspected of having an iron-related pathology is indicative of enhanced coagulation and/or diminished fibrinolysis compared to the viscoelastic parameters of the blood sample from the healthy subject.

3. The method of claim 1, wherein the viscoelastic parameter is TMRTG.

4. The method of claim 1, wherein at least one of the viscoelastic parameters is at least 10, 20, 30, 40, or 50% higher than the same viscoelastic parameter of a plasma samples from healthy subjects, indicating that the subject has an iron-related pathology.

5. The method of claim 4, wherein both viscoelastic parameters are at least 10, 20, 30, 40, or 50% higher than the same viscoelastic parameter of a plasma samples from healthy subjects, indicating that the subject has an iron-related pathology.

6. The method of claim 3, wherein the subject is diagnosed with an iron-related pathology when the viscoelastic parameters are at least 10, 20, 30, 40, or 50% higher than the viscoelastic parameters of a blood sample from a healthy subject.

7. The method of claim 1, wherein the iron-related pathology is selected from the group consisting of biomaterial-blood interaction during mechanical circulatory support, heme-oxygenase overexpression, bacterial infection, inflammatory disorders associated with thrombophilia, diabetes mellitus, rheumatoid arthritis; sickle-cell anemia, thyroid cancer, breast cancer, brain cancer, thoracic cancer, colon cancer, pancreatic cancer, hemolysis, iron overload, iatrogenic iron increases in plasmatic iron concentration, hemochromatosis, and chronic hyperferritinemia.

8. The method of claim 1, wherein the viscoelastic parameter is MRTG.

9. The method of claim 1, wherein the iron specific chelator is selected from the group consisting of deferoxamine, deferiprone, deferasirox, desferrithiocin (S)-desmethyldesferrithiocin (DMDFT), desferri-exochelin, ICL670A, CP94, tachpyridine, tachpyridine analogs, aroylhydrazones, 2-pyridylcarboxaldehyde isonicotinoyl hydrazone analogs, di-2-pyridylketone isonicotinoyl hydrazone analogs, triapine, 2-hydroxy-1-naphthylaldehyde-3-thiosemicarbazone (NT), 2-hydroxy-1-naphthaldehyde-4,4-dimethyl-3-thiosemicarbazone (N44mT), N2mT, N4mT, 2-hydroxy-1-naphthaldehyde-4-ethyl-3-thiosemicarbazone (N4eT), 2-hydroxy-1-naphthaldehyde-4-allyl-3-thiosemicarbazone (N4aT), 2-hydroxy-1-naphthaldehyde-4-phenyl-3-thiosemicarbazone (N4pT), DpT, Dp2mT, di-2-pyridylketone-4-methyl-3-thiosemicarbazone (Dp4mT), Dp44mT, di-2-pyridylketone-4-ethyl-3-thiosemicarbazone (Dp4eT), di-2-pyridylketone-4-allyl-3-thiosemicarbazone (Dp4aT), and di-2-pyridylketone-4-phenyl-3-thiosemicarbazone (Dp4pT), di-2-pyridylketone-4,4,-dimethyl-3-thiosemicarbazone (Dp44mT), and combinations thereof.

10. The method of claim 9, wherein the iron specific chelator is deferoxamine.

11. The method of claim 1 wherein the sample is incubated in a plastic cup, and optionally, wherein the sample is anticoagulated with sodium citrate.

12. The method of claim 11 wherein the incubation time is between 15 minutes and sixty minutes and optionally, wherein the viscoelastic parameters are obtained using thromboelastographic or thromboelastometric methods.

13. The method claim 12, wherein the sample is incubated with the iron chelator at 37° C.

14. The method of claim 10 wherein the sample is incubated with deferoxamine for 15 minutes at 37° C.

15. The method of claim 12, wherein the sample is incubated with the iron chelator at room temperature.

16. The method of claim 1 wherein a variation the viscoelastic parameter of the sample in the absence of an iron chelator outside the normal 95% Confidence Interval is indicative of hypercoagulability.

17. The method of claim 1 wherein a decrease in MRTG>1.2 dynes/cm2/sec after incubation of the sample with the iron chelator is indicative of iron mediated enhancement of coagulation.

\* \* \* \* \*